United States Patent
Liao et al.

(10) Patent No.: US 11,358,136 B2
(45) Date of Patent: Jun. 14, 2022

(54) AMPHOTERIC DISSOCIATION ION EXCHANGE MEDIUM AND USES THEREOF AND METHOD FOR CALIBRATING SEPARATION CAPACITY THEREOF

(71) Applicant: CHONGQING BOLANYING (BLY) BIOTECHNOLOGY CO., LTD., Chongqing (CN)

(72) Inventors: Fei Liao, Chongqing (CN); Gaobo Long, Chongqing (CN); Yanling Xie, Chongqing (CN); Mingtong Huang, Chongqing (CN); Wanjun Xie, Chongqing (CN)

(73) Assignee: CHONGQING BOLANYING (BLY) BIOTECHNOLOGY CO., LTD., Chongqing (CN)

( * ) Notice: Subject to any disclaimer, the term of this patent is extended or adjusted under 35 U.S.C. 154(b) by 0 days.

(21) Appl. No.: 16/902,564

(22) Filed: Jun. 16, 2020

(65) Prior Publication Data
US 2020/0376480 A1 Dec. 3, 2020

Related U.S. Application Data

(60) Division of application No. 16/435,515, filed on Jun. 9, 2019, now abandoned, and a continuation of
(Continued)

(30) Foreign Application Priority Data

Oct. 25, 2017 (CN) .......................... 201711010305.0

(51) Int. Cl.
*B01J 43/00* (2006.01)
*B01J 47/014* (2017.01)
(Continued)

(52) U.S. Cl.
CPC ............ *B01J 43/00* (2013.01); *B01J 47/014* (2017.01); *C07K 1/18* (2013.01); *C12N 15/101* (2013.01);
(Continued)

(58) Field of Classification Search
CPC ........... B01J 43/00; B01J 47/014; C07K 1/18; C12N 15/101; C12Q 1/6806;
(Continued)

(56) References Cited

U.S. PATENT DOCUMENTS

| | | | |
|---|---|---|---|
| 7,402,390 B2 * | 7/2008 | Hwang | ................ B01D 15/364 435/6.12 |
| 2001/0014650 A1 * | 8/2001 | Smith | ...................... B01J 39/26 502/401 |
| 2007/0241056 A1 * | 10/2007 | Klipper | .............. B01J 20/28085 210/660 |

* cited by examiner

*Primary Examiner* — Benjamin L Lebron

(57) ABSTRACT

An amphoteric dissociation ion exchange separation medium, the surface of which is an amphoteric dissociation covalently-modified layer. When an environmental pH value is lower than the isoelectric point, pIm, of the covalently-modified layer, the type of net charges on the surface of the covalently-modified layer is positive and the separation medium has the properties of an anion exchanger; when the environmental pH value is higher than the pIm, the type of net charges on the covalently-modified layer surface is negative and the separation medium has the properties of a cation exchanger. The separation medium has the properties of an anion exchanger and a cation exchanger at both sides of the pIm, respectively. The pH of an eluent can be adjusted to allow the separation medium surface and the target substance to have the same type of net charges, so that the target substance can be released by electrostatic repulsion.

1 Claim, 8 Drawing Sheets

Related U.S. Application Data application No. PCT/CN2018/111536, filed on Oct. 24, 2018.

(51) Int. Cl.
*C07K 1/18* (2006.01)
*G01N 1/40* (2006.01)
*G01N 21/31* (2006.01)
*G01N 21/80* (2006.01)
*C12N 15/10* (2006.01)
*C12Q 1/6806* (2018.01)

(52) U.S. Cl.
CPC ......... *C12Q 1/6806* (2013.01); *G01N 1/4005* (2013.01); *G01N 21/31* (2013.01); *G01N 21/80* (2013.01); *G01N 2001/4011* (2013.01)

(58) Field of Classification Search
CPC ...... G01N 1/4005; G01N 21/31; G01N 21/80; G01N 2001/4011
See application file for complete search history.

AMPHOTERIC DISSOCIATION ION EXCHANGE MEDIUM AND USES THEREOF AND METHOD FOR CALIBRATING SEPARATION CAPACITY THEREOF

CROSS-REFERENCE TO RELATED APPLICATIONS

This application is a divisional application of U.S. patent application Ser. No. 16/435,515, filed on Jun. 9, 2019, which is a continuation of International Patent Application No. PCT/CN2018/111536, filed on Oct. 24, 2018, claiming the benefit of priority from Chinese Application No. 201711010305.0, filed on Oct. 25, 2017. The entire contents of the aforementioned applications, including any intervening amendments thereto, are incorporated herein by reference.

TECHNICAL FIELD

The application relates to an ion-exchange medium for separation of biologically active substances, and more particularly to an amphoteric dissociation ion exchange medium and uses thereof and a method for calibrating separation capacity thereof.

BACKGROUND

Ion exchange media are suitable for fast separation and analysis of biomolecules such as proteins and nucleic acids, purification and preparation of proteins and nucleic acids, and chromatographic quantitative analysis of charged substances. These applications require that the ion exchange media have high adsorption capacity, high elution efficacy to the adsorbed substances under mild conditions, accurate calibration of separation capacity, low non-specific adsorption of interfering substances and high regeneration ability under mild conditions. Since classical ion exchange media cannot meet the above requirements simultaneously, the invention is intended to design a novel ion exchange medium that meets the requirements as much as possible.

Under a given pH, surface groups of the separation medium dissociate and form ion pairs through electrostatic attraction with counter ions of small size, and then the oppositely charged target substances are absorbed based on electrostatic attraction and competitive binding to perform on-line chromatographic analysis of the target substances, or further, the adsorbed target substances are eluted by competitive ions provided by high concentration of monovalent neutral inorganic salts such as NaCl and KCl based on electrostatic attraction and competitive binding. This is called ion exchange, and the separation media used are known as ion exchangers.

The pH for ion exchange separation of biomolecules is usually between 5.0 and 8.0, and is generally limited to between 3.0 and 11.0. When the target substance is purified or extracted by classical ion exchangers, both the adsorption and elution rely on properties of the target substance, charged groups on the surface of the separation medium, and the electrostatic attraction and competitive binding between ions in the solution. There is usually only one type of ionizable groups on the surface of the classical ion exchange separation medium, and there are only two types of surface net charges at pH from 3.0 to 11.0. An ion exchange separation medium of which the surface net charge is positive or zero but not negative is called an anion exchanger; and conversely, an ion exchange separation medium of which the surface net charge is negative or zero but not positive is called a cation exchanger. There are still some defects in the performance of the classical ion exchangers for purification, preparation, extraction, concentration and chromatographic analysis of biomolecules. First, for good hydrophilicity, the classical ion exchangers are provided with a large amount of hydrogen bond-forming groups such as hydroxyl groups and amides, but such groups may form considerable hydrogen bonds with the target substance to generate non-specific adsorption, reducing the elution efficacy of the proteins/nucleic acids adsorbed by the classical ion exchangers, separation selectivity and capacity, and regeneration efficacy. Second, for a desirable elution efficacy, the monovalent neutral inorganic salt should be at a high concentration when used to promote the release of the target substance by competitive binding, and the desalting is further required before the subsequent reanalysis/treatment, lowering the efficiency and increasing the cost. Therefore, there is a need to develop an ion exchange separation medium based on a new principle, which can not only significantly reduce non-specific adsorption but also improve the elution efficacy of the adsorbed target substance.

The classical ion exchangers cannot be applied to nucleic acid extraction, concentration and reanalysis due to low elution efficacy. Nucleic acids, as the genetic material, play crucial roles in biomedical analyses such as the current clinical diagnosis of infectious diseases, forensic evidence detection, genotyping, food safety detection, and confirmation of sources of pharmaceutical raw materials. Nucleic acids have low contents in biological samples and are usually detected after PCR amplification. However, there are often a large number of non-nucleic acid substances in the samples that interfere with PCR amplification of nucleic acids. Therefore, rapid extraction of nucleic acids from the samples and removal of most interfering substances must be simultaneously performed before the PCR amplification. Nucleic acids have phosphodiester bonds, and are dissociated to polyanion with negative net charges at pH above 2.0, so the anion exchanger can theoretically be used for nucleic acid extraction, concentration and analysis. Conventional anion exchangers have high adsorption capacity for nucleic acids, but how to elute the adsorbed nucleic acids is technically challenging. A monovalent neutral inorganic salt at high concentration scan be used to improve the elution efficacy of the adsorbed nucleic acid anions, while the excessive inorganic salt may inhibit the subsequent PCR amplification. Currently, therapid extraction of nucleic acids in the samples for analysis uses silanol as an adsorption group by forming hydrogen bonds under mild conditions to ensure the elution efficacy. In addition, in order to improve the reproducibility of nucleic acid extraction to ensure the reproducibility of nucleic acid analysis, micro-magnetic beads are commonly used for rapid adsorption, separation and elution of nucleic acids. However, the silanol has low nucleic acid-binding capacity and low selectivity to nucleic acids, resulting in the use of a large amount of silanol magnetic beads at high cost. Many impurities may also be adsorbed and eluted in the nucleic acid elution due to high non-specific adsorption of the surface of silanol magnetic beads, thereby inhibiting the PCR and affecting the sensitivity of nucleic acid detection. Ion exchange is also a conventional method for protein purification, but in this application, the target protein often has a low elution yield even if a monovalent neutral inorganic salt is used at a high concentration for competitive elution. Moreover, the inorganic salt requires to be removed by dialysis or ultrafiltration before subsequent operations/analyses, reducing the operation efficiency and increasing the cost. Therefore, there is a need to develop novel ion exchangers for rapid extraction/purification and preparation of nucleic acids and proteins to improve the elution efficacy of the adsorbed substance with a low ionic-strength buffer.

After the target substance is adsorbed on the surface of the ion exchange medium by electrostatic attraction, the ion exchange medium can be treated by an eluent with significantly different pH to have a surface net charge of zero, thereby enhancing the elution efficacy of the target substance. However, a large amount of hydrogen bonds between the target substance and the ion exchange medium still retard the elution, and the non-specific adsorption of common ion exchange mediums to interfering small molecules on common ion exchange media may interfere with the subsequent analyses. The generation of electrostatic repulsion between the adsorbed target substance and the ion exchange medium can certainly promote the elution of the adsorbed target substance and the regeneration of the separation medium. An eluent with pH significantly different from that of an adsorption buffer is expected to generate electrostatic repulsion between the target substance and the surface of the separation medium. However, there is only one type of dissociable groups on the surface of any one classic ion exchanger, so that the opposite charge between the net charge on the surface of the separation medium and the net charge of the target substance cannot be easily changed to the same by adjusting the elution pH, thereby failing to generate electrostatic repulsion and promote elution.

Therefore, in order to overcome the defects of classical ion exchange separation medium in the separation of biomolecules, there is a need to develop a novel ion exchange medium that provides high adsorption capacity, high elution efficacy of the adsorbed substance under mild conditions, separation capacity which can be accurately and easily calibrated, low non-specific adsorption of non-target substances and high regeneration efficacy.

SUMMARY

In view of the above, the application provides a novel ion exchange medium with high-efficiency adsorption, large adsorption capacity, high-efficacy elution of adsorbed ions under mild conditions, easy accurate calibration of separation capacity, low non-specific adsorption of non-target substances and high regeneration ability under mild conditions.

The application provides an amphoteric dissociation ion exchange separation medium, wherein a surface of the amphoteric dissociation ion exchange separation medium is an amphoteric dissociation covalently-modified layer; the amphoteric dissociation covalently-modified layer has an isoelectric point, denoted as pIm, and the isoelectric point is an environmental pH value at which the net charge on the surface of the amphoteric dissociation ion exchange separation medium is zero; wherein, when the environmental pH value is lower than the pIm, the net charge on the surface of the amphoteric dissociation covalently-modified layer is positive and the amphoteric dissociation ion exchange separation medium has the properties of an anion exchanger; when the environmental pH value is higher than the pIm, the net charge on the surface of the amphoteric dissociation covalently-modified layer is negative and the amphoteric dissociation ion exchange separation medium has the properties of acation exchanger.

In an embodiment, when the environmental pH value is lower than the pIm, the number of positive net charge on the surface of the amphoteric dissociation covalently-modified layer gradually increases as the difference between the pIm and the environmental pH value increases; when the environmental pH value is higher than the pIm, the number of negative net charge on the surface of the amphoteric dissociation covalently-modified layer gradually increases as the difference between the pIm and the environmental pH value increases. Clearly, the environmental pH value is located in a pH range which is tolerated by both a target substance to be separated and the amphoteric dissociation ion exchange separation medium.

In an embodiment, the amphoteric dissociation covalently-modified layer on the surface of the amphoteric dissociation ion exchange separation medium simultaneously comprises a group which dissociates to generate positive charge when pH is lower than the pIm, and a group which dissociates to generate negative charge when pH is higher than the pIm; and the group which dissociates to generate negative charge is an aliphatic carboxyl group, and the group which dissociates to generate positive charge is one or more groups selected from the group consisting of an aliphatic primary amine group, an aliphatic secondary amine group, an aliphatic tertiary amine group and an imidazolyl group.

In an embodiment, the amphoteric dissociation covalently-modified layer is derived from covalent modification of the surface of a separation medium substrate by an amphoteric dissociation group precursor;

the surface of the separation medium substrate does not contain a linear long chain having a length more than 9 atoms, but contains a reactive group for covalently linking with the amphoteric dissociation group precursor to form the amphoteric dissociation covalently modified layer; the reactive group is any one group selected from the group consisting of an aliphatic primary amine group, an aliphatic secondary amine group, an aliphatic carboxyl group and a thiol reactive group; wherein the thiol reactive group contains a small-size group that is substituted by a thiol and leaves from the surface of the separation medium substrate;

the amphoteric dissociation group precursor is a hydrophilic material having a molecular weight less than 500 Daltons and no hydrocarbon chains or hydrocarbon rings with more than 5 successive carbon atoms; wherein the amphoteric dissociation group precursor contains an alkylthiol group or an aliphatic primary amine group as a covalently-linking group and an aliphatic carboxyl group as a group which dissociates to generate negative charge, and/or one or more groups selected from the group consisting of an aliphatic primary amine group, an aliphatic secondary amine group, an aliphatic tertiary amine group and an imidazolyl group as a group which dissociates to generate positive charge; the amphoteric dissociation group precursor comprises a type A precursor, a type B precursor and a type C precursor, wherein the type A precursor is an amphoteric dissociation group precursor comprising only the group which dissociates to generate negative charge besides the covalently-linking group, the type B precursor is an amphoteric dissociation group precursor comprising only the group which dissociates to generate positive charge besides the covalently-linking group, and the type C precursor is an amphoteric dissociation group precursor comprising the group which dissociates to generate negative charge and the group which dissociates to generate positive charge besides the covalently-linking group; and the separation medium substrate is covalently modified with the amphoteric dissociation group precursor by one of the following methods:

a) using the type C precursor alone or in combination; wherein when used in combination, various type C precursors are mixed at a given ratio for use, and the precursors for mixing contain the same covalently-linking group;

b) mixing one or more type A precursors with one or more type B precursors at a given ratio for use; wherein these precursors for mixing contain the same covalently-linking group;

c) mixing only one or more type A precursors with one or more type C precursors in a given ratio; wherein these precursors for mixing contain the same covalently-linking group; and d) mixing only one or more type B precursors with one or more type C precursors in a given ratio; wherein these precursors for mixing contain the same covalently-linking group.

In an embodiment, when the amphoteric dissociation group precursor is used to covalently modify the separation medium substrate, a molar ratio of the total amount of aliphatic primary, secondary, tertiary amine groups and imidazolyl groups to the total amount of aliphatic carboxyl groups in the amphoteric dissociation group precursor is limited to 1:6 to 6:1.

In an embodiment, when an aliphatic secondary amine and/or an aliphatictertiary amine are/is used in an amphoteric dissociation group precursor as the group which dissociates to generate positive charges, the total molar amount of the aliphatic secondary amine and the aliphatictertiary amine does not exceed 30% of the total molar amount of the aliphatic primary amine and theimidazolyl group in precursors used.

In an embodiment, the number of positive charges on the surface of the amphoteric dissociation ion exchange separation medium is not less than 90% of the maximum value at pH 3, and the number of negative charge on the surface of the amphoteric dissociation ion exchange separation medium is not less than 90% of the maximum value at pH 11.

The application further discloses a use method of the amphoteric dissociation ion exchange separation medium, comprising:

applying the amphoteric dissociation ion exchange separation medium to separate a target substance; wherein a common logarithm of a dissociation constant obtained from the release of hydrogen ion from the target substance is pK or an isoelectric point of the target substance is p; wherein the method further comprises:

a. selecting an amphoteric dissociation ion exchange separation medium; wherein the difference between the pIm of the amphoteric dissociation ion exchange separation medium and the pK or pI of the target substance is not less than 1.0;

b. adsorbing the target substance; wherein an environment pH is selected to allow the type of net charges on the surface of the ion exchange separation medium to be opposite to the type of net charges of the target substance, thereby resulting in adsorption of the target substance by electrostatic attraction, wherein the environmental pH is located between the pK or pI of the target substance and the pIm of the amphoteric dissociation ion exchange separation medium and the difference between the environmental pH and the pK or pI of the target substance and the difference between the environmental pH and the pIm of the amphoteric dissociation ion exchange separation medium are both greater than 0.3; and c. eluting the target substance; wherein when pH of an eluent is lower than the pIm of the amphoteric dissociation ion exchange separation medium, the pH of the eluent is at least 0.3 lower than the lower one of the pK or pI of the target substance and the pIm of the amphoteric dissociation ion exchange separation medium; when the pH of the eluent is higher than the pIm of the amphoteric dissociation ion exchange separation medium, the pH of the eluent is at least 0.3 higher than the higher one of the pK or pI of the target substance and the pIm of the amphoteric dissociation ion exchange separation medium; in the use of the above eluent, the type of net charges of the surface of the amphoteric dissociation ion exchange separation medium is the same as that of the target substance, thereby resulting in elution of the target substance by electrostatic repulsion; and a water-soluble monovalent neutral inorganic salt is added to the eluent to promote the elution of the target substance.

The application also discloses a method for calibrating separation capacity of the amphoteric dissociation ion exchange separation medium, comprising:

a) selecting an colored organic compound as a color-developing probe for the calibration of the separation capacity of the amphoteric dissociation ion exchange separation medium; wherein the colored organic compound has a dissociation constant of pK or an isoelectric point of pI, a molecular weight less than 600 Daltons, a visible light absorption coefficient greater than 14 $mM^{-1}$ $cm^{-1}$, a solubility not less than 5.0 μmol/L at pH 3.0-11.0, and a positive or negative net charge after dissociation at pH 3.0-11.0;

b) calibrating the separation capacity of the amphoteric dissociation ion exchange separation medium; wherein step b comprises:

b1) when the amphoteric dissociation ion exchange separation medium has an isoelectric point pIm between 4.0 and 6.0, using a cationic probe with a dissociation constant of pK or an isoelectric point of pI at least 2.0 greater than the pIm of the amphoteric dissociation ion exchange separation medium, or using an anionic probe with a dissociation constant of pK or an isoelectric point of pI at least 2.0 lower than the pIm of the amphoteric dissociation ion exchange separation medium; and b2) when the amphoteric dissociation ion exchange separation medium has the pIm between 6.0 and 10.0, using the anionic probe with a dissociation constant of pK or an isoelectric point pI at least 2.0 lower than the pIm of the amphoteric dissociation ion exchange separation medium;

c) when calibrating the separation capacity of the amphoteric dissociation ion exchange separation medium, selecting a buffer solution corresponding to an environmental pH to allow the amphoteric dissociation ion exchange separation medium to adsorb a color-developing probe by electrostatic attraction, wherein the environmental pH is between the dissociation constant pK or the isoelectric point pI of the color-developing probe and the pIm of the amphoteric dissociation ion exchange separation medium, and differs from the pIm of the amphoteric dissociation ion exchange separation medium by not less than 1.3 and differs from the dissociation constant pK or the isoelectric point pI of the color-developing probe by not less than 0.5; selecting a buffer solution corresponding to an environmental pH to allow the type of net charges on the surface of the amphoteric dissociation ion exchange separation medium to be the same as that of the color-developing probe in the elution, thereby eluting a color-developing probe by electrostatic repulsion, wherein the environmental pH is at least 1.3 higher than the higher one or at least 1.3 lower than the lower one of the dissociation constant pK or the isoelectric point pI of the color-developing probe and the pIm of the amphoteric dissociation ion exchange separation medium; measuring the adsorption of a color-developing probe in an eluate followed by conversion into a separation capacity for the color-developing probe; and determining pH effect on the separation capacity of the amphoteric dissociation ion exchange separation medium to a color-developing probe; wherein the minimum pH at which the separation capacity for the color-developing probe with negative net charge reaches zero, or the maximum pH at which the separation capacity for the color-developing probe with positive net charge reaches zero, is an approximation of the pIm of the amphoteric dissociation ion exchange separation medium.

The application has the following beneficial effects.

The invention provides an amphoteric dissociation ion exchange separation medium, where covalent modification is adopted to form a structure of amphoteric dissociation covalently-modified layer on the surface of the medium and a specific isoelectric point pIm is formed according to the difference in the modified structure or the proportion of the amphoteric dissociation group precursors. In addition, the separation medium has the properties of an anion exchanger and a cation exchanger, respectively, at different environmental pHs on both sides of the pIm. The ion exchange property of the amphoteric dissociation ion exchange separation medium can be reversed by changing a pH at one side of the pIm into a pH at the other side of the pIm, thereby providing significantly different adsorption and separation effect on the charged substance as the pH crosses the pIm. pH of a buffer solution can be adjusted to allow the surface of the amphoteric dissociation ion exchange separation medium of the invention and the target substance to have the same net charge, so that the target substance can be released by electrostatic repulsion, thereby enhancing the elution efficacy, especially increasing the elution rate and improving the regeneration property of the separation medium, and avoiding the subsequent problem caused by using high-concentration inorganic ions. The competitive binding between ions is no longer necessary in the elution, but can still be used to promote the elution. In summary, the amphoteric dissociation ion exchange separation medium of the invention has both electrostatic interaction-based adsorption and electrostatic interaction-based elution performances, and also provides high separation capacity, high-efficacy elution of adsorbed ions under mild conditions, easy accurate calibration of separation capacity, low non-specific adsorption to non-target substances and high regenerative efficiency under mild conditions. Furthermore, the invention employs special amphoteric dissociation group precursors to covalently modify a separation medium substrate to form the desired amphoteric dissociation covalently-modified layer, allowing the separation medium surface for an amphoteric dissociation property. This formation method has the following beneficial effects. First, this strategy makes it easier to adjust the molar ratio of a group dissociating to form an anion to a group dissociating to form a cation to obtain different pIm favorable for the adsorption of different biomolecules. It is apparent that this strategy is simpler and more practical, and involves higher efficiency when compared to the direct preparation of a separation medium with an amphoteric dissociation group on the surface by adjusting the polymerization conditions. Secondly, a natural cellulose-polymer separation medium is suitable as a substrate to prepare an amphoteric dissociation ion exchange separation medium by such a method. It should be noted that the existing technology fails to prepare the cellulose by polymerization, let alone directly prepare a cellulose with an amphoteric dissociation group on the surface by polymerization. Furthermore, this method facilitates the selection of a separation medium satisfying specific requirements as a substrate for covalent modification to obtain the amphoteric dissociation surface, which is advantageous for avoiding reduction in coverage of amphiphilic dissociation groups on the surface caused by steric hindrance between charged groups during polymerization, thereby ensuring high coverage of hydrophilic groups on the surface and reducing non-specific adsorption to hydrophobic small molecules. In other words, this formation method plays two important roles respectively in forming the desired amphoteric dissociation group on the surface and in reducing non-specific adsorption of the surface to hydrophobic substances, allowing the amphoteric dissociation ion exchange separation medium for a better performance.

The application further discloses a use method of the amphoteric dissociation ion exchange separation medium and a method for calibrating the separation capacity of the amphoteric dissociation ion exchange separation medium. The use method is simple and only requires a color-developing probe with a specific pK or pI. The process of calibrating the separation capacity is simple and rapid, and the measurement of the absorbance of the probe is easy to be standardized and has good reproducibility. Therefore, this calibration method is suitable for the standard setting and tracing of product quality and characterization of the amphoteric dissociation property of the amphoteric dissociation ion exchange separation medium, thereby providing rapid, simple and high-accuracy calibration of the separation capacity of the ion exchange separation medium and characterization of its properties.

BRIEF DESCRIPTION OF THE DRAWINGS

The present invention will be further described below with reference to the drawings and embodiments.

DETAILED DESCRIPTION OF EMBODIMENTS

Figure 1:
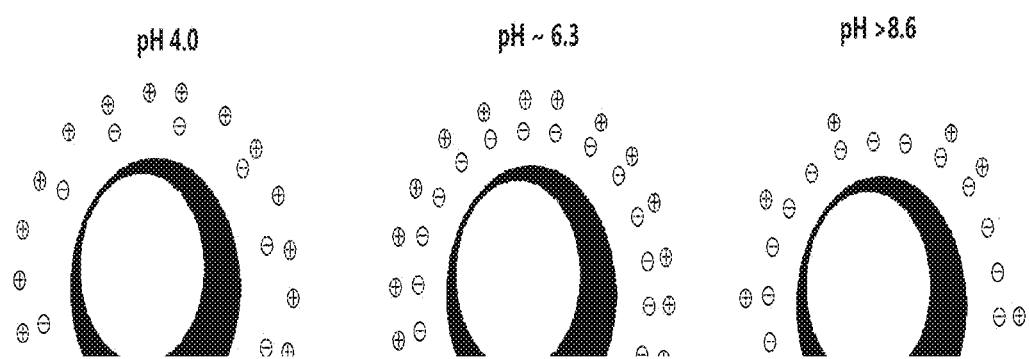
FIG. 1 shows the change in surface net charge of FBD-MSP-ZEW with pH.

Provided in the embodiments is an amphoteric dissociation ion exchange separation medium, where the surface of the amphoteric dissociation ion exchange separation medium is an amphoteric dissociation covalently-modified layer; the amphoteric dissociation covalently-modified layer has an isoelectric point (pIm), and the pIm is an environmental pH value at which the net charge on the surface of the amphoteric dissociation ion exchange separation medium is zero; when the environmental pH value is lower than the pIm, the net charge on the surface of the amphoteric dissociation covalently-modified layer is positive and the amphoteric dissociation ion exchange separation medium has the properties of an anion exchanger; when the environmental pH value is higher than the pIm, the net charge on the surface of the amphoteric dissociation covalently-modified layer is negative and the amphoteric dissociation ion exchange separation medium has the properties of acation exchanger. The amphoteric dissociation covalently-modified layer contains an amphoteric dissociation substance which contains both a group dissociating to generate negative charge and a group dissociating to generate positive charge. The electrostatic attraction between the separation medium bearing an amphoteric dissociation covalently-modified layer on the surface and the target substance can be reversed to electrostatic repulsion using adsorption and elution buffer solutions with a significant difference in pH, enabling efficient elution based on electrostatic repulsion. In a pH range that the separation medium and the target substance can tolerate, this novel elution based on electrostatic repulsion can be performed by adjusting the pH to change the net charge type of the surface of the separation medium and keep the net charge type of the target substance unchanged, or to change the net charge type of the target substance and keep the net charge type of the separation medium unchanged. The pH range that the bioactive substance can tolerate is limited. Unless the target substance is an amphoteric dissociation substance, its charge type cannot be reversed, thereby failing to reverse the electrostatic interaction between the target substance and the separation medium surface from attraction to repulsion. In order to make it applicable for both the amphoteric dissociation target substance and the non-amphoteric dissociation target substance, there is a need to develop a novel ion exchange separation medium of which the net charge type can be changed by adjusting pH in a limited range, that is, an ion exchange separation medium with an amphoteric dissociation modification layer on its surface (as shown in FIG. 1).

The charge type of an amphoteric dissociation substance is often characterized by a pH at which its net charge is zero, that is, the isoelectric point p, while the charge type of a non-amphoteric dissociation substance is often characterized by its dissociation constant pK. For convenience, the isoelectric point of the amphoteric dissociation target substance is also called pIs and a pH at which the surface net charge of the ion exchange separation medium is zero, i.e., the isoelectric point, is called pIm. Stronger hydrophilicity of the surface of the ion exchange separation medium may result in lower non-specific adsorption to most substances, especially the uncharged hydrophobic substances, which is beneficial to improve the regeneration efficacy and separation selectivity of such separation medium, thereby improving the sensitivity of subsequent analysis. However, to achieve the reversal from efficient adsorption of the target substance to the separation medium surface based on electrostatic attraction to efficient elution of the target substance from the separation medium surface based on electrostatic repulsion by adjusting pH, the pIm of the amphoteric dissociation ion exchange separation medium is also required to meet the following conditions: in a pH range which the target substance and the separation medium can tolerate, the net charge of the separation medium surface is positive at a lower pH and can be reversed to negative at a higher pH, which indicates that the pIm of the separation medium is required to be in the middle of the pH range which both the target substance and the separation medium can tolerate; in addition, for an amphoteric dissociation target substance, it is also required that there is sufficiently large difference between the pIm of the suitable ion exchange separation medium and the pIs of the target substance. After meeting such conditions, pH of the adsorption buffer is selected to allow the net charge of the target substance to be opposite to that of the separation medium surface to provide electrostatic adsorption, thereby minimizing the non-specific adsorption of interfering substances by washing the separation medium after the adsorption of the target substance by the adsorption buffer. Then, a buffer with a suitable pH is used to allow the net charge of the target substance to be the same as that of the separation medium surface to provide electrostatic repulsion, thereby efficiently eluting the target substance. A water-soluble monovalent neutral inorganic salt may be added to promote the elution. This ion exchange separation medium exhibits significant advantages in extracting and concentrating a charged target substance, so that it may have a longer life and higher separation efficacy when used as an ion exchange chromatography column packing material, or provide higher regeneration efficacy, simple and rapid separation and higher yield of the target substance when used in the preparation of the target substance.

The adsorption and elution of the target substance on the surface of the ion exchange separation medium are achieved by adjusting pH, where the principle of the elution in the use of this separation medium is significantly different from that in the use of the classical ion exchanger. In the use of such ion exchange separation medium, the surface of the separation medium and the target substance can have the same type of net charges by adjusting the elution pH, so that electrostatic repulsion is generated to promote the release of the target substance, thereby improving the elution efficacy, especially increasing the elution rate and elution percentage of the adsorbed target substance, and avoiding the subsequent problems caused by high-concentration inorganic ions. In the elution, the competitive binding between ions is no longer necessary, but can still be introduced to promote the elution. The adsorption and separation of the targeted substance with the amphoteric dissociation ion exchange separation medium at a pH which is at one side of the pIm are significantly different from those at a pH which is at the other side of the pIm. Specifically, the separation medium adsorbs anions at a pH lower than the pIm, that is, playing a role as an anion exchanger; the separation medium adsorbs cations at a pH higher than the pIm, that is, playing a role as a cation exchanger. Obviously, the adsorption of the charged substance on the classical ion exchanger cannot be reversed by the adjustment of pH.

When the environmental pH value is lower than the pIm of the amphoteric dissociation ion exchange separation medium, the number of positive charges on the surface of the amphoteric dissociation covalently-modified layer gradually increases as the difference between the pIm and the environmental pH value increases; when the environmental pH value is higher than the pIm, the number of negative charges on the surface of the amphoteric dissociation covalently-modified layer gradually increases as the difference between the pIm and the environmental pH value increases. The environmental pH value is located in a pH range which is tolerated by both a target substance and the amphoteric dissociation ion exchange separation medium.

In this embodiment, the amphoteric dissociation covalently-modified layer on the surface of the amphoteric dissociation ion exchange separation medium comprises simultaneously a group which dissociates to generate positive charge when pH is lower than the pIm, and a group which dissociates to generate negative charge when pH is higher than the pIm. The group which dissociates to generate negative charge is an aliphatic carboxyl group, and the group which dissociates to generate positive charge is one or more groups selected from the group consisting of an aliphatic primary amine group, an aliphatic secondary amine group, an aliphatic tertiary amine group and an imidazolyl group.

In this embodiment, the amphoteric dissociation covalently-modified layer is derived from covalent modification of the surface of a separation medium substrate by an amphoteric dissociation group precursor.

The separation medium substrate is a particle of any size or a film of any thickness that does not contain a linear long chain having a length more than 9 atoms, but contains any one of the following reactive groups for covalently linking with the amphoteric dissociation group precursors to form the amphoteric dissociation covalently modified layer: an aliphatic primary amine group, an aliphatic secondary amine group, an aliphatic carboxyl group and a thiol reactive group; where the thiol reactive group contains a small-size group that is substituted by a thiol and leaves from the surface of the separation medium substrate.

The amphoteric dissociation group precursor is a hydrophilic material having a molecular weight less than 500 Daltons and nohydrocarbon chains or hydrocarbon rings with more than 5 successive atoms. The amphoteric dissociation group precursor contains an alkylthiol group or an aliphatic primary amine group for covalent linking and an aliphatic carboxyl group as a group which dissociates to generate negative charge, and/or one or more groups selected from the group consisting of an aliphatic primary amine group, an aliphatic secondary amine group, an aliphatic tertiary amine group and an imidazolyl group, as a group which dissociates to generate positive charge. The amphoteric dissociation group precursor comprises a type A precursor, a type B precursor and a type C precursor. The type A precursor is an amphoteric dissociation group precursor comprising only the group which dissociates to generate negative charge besides the covalently-linking group. The type B precursor is an amphoteric dissociation group precursor comprising only the group which dissociates to generate positive charge besides the covalently-linking group. The type C precursor is an amphoteric dissociation group precursor comprising the group which dissociates to generate negative charge and the group which dissociates to generate positive charge besides the covalently-linking group. The type C precursor comprises lysine, ornithine, histidine,N,N-dicarboxymethylethylenediamine, cysteine, 3-thiolhistidine, 3-thiol lysine and 3-thiol glutamic acid; the type A precursor comprises glutamic acid, 3-thiol-1,5-glutaric acid, thioglycolic acid and tris-(carboxymethyl)-aminomethane; and the type B precursor comprises mercaptoethylamine, 3-thiol-2-hydroxypropylamine, 2-mercaptoimidazole,diethylenetriamine,N,N-dimethylaminoethylenediamine and tetra-(aminomethyl)-methane. These substances may be used alone or in combination of two or more of them to adjust the ratio of the group which dissociates to generate positive charges to the group which dissociates to generate negative charges, thereby adjusting pIms of the amphoteric dissociation ion exchange separation mediums.

The separation medium substrate is covalently modified with the amphoteric dissociation group precursor(s) by one of the following methods:

a) using the type C precursor alone or in combination; wherein when used in combination, various type C precursors are mixed at a given ratio for use, and the precursors for mixing contain the same type of groups for covalent linking;

b) mixing one or more type A precursors with one or more type B precursors in a given ratio for use; wherein these precursors for mixing contain the same type of groups for covalent linking;

c) mixing only one or more type A precursors with one or more type C precursors in a given ratio; wherein these precursors for mixing contain the same type of groups for covalent linking; and d) mixing only one or more type B precursors with one or more type C precursors in a given ratio; wherein these precursors for mixing contain the same type of groups for covalent linking.

When the amphoteric dissociation group precursor is used to covalently modify the separation medium substrate, the molar ratio of the total amount of aliphatic primary, secondary, tertiary amine groups and imidazolyl groups to the total amount of aliphatic carboxyl groups in the amphoteric dissociation group precursor(s) is limited to 1:6 to 6:1. When an aliphatic secondary amine and/or an aliphatic tertiary amine are/is used in an amphoteric dissociation group precursor as the group which dissociates to generate positive charge, the total molar amount of the aliphatic secondary amine and the aliphatic tertiary amine does not exceed 30% of the total molar amount of the aliphatic primary amine and the imidazolyl group.

There are two kinds of covalent-linking reactions: amide formation between the aliphatic amine group and the aliphatic carboxyl group, and substitution of a leaving group by an alkyl thiol.

There is no amphoteric dissociation covalently-modified layer and no long linear groups with more than 9 atoms on the surface of the separation substrate. When the separation medium without the amphoteric dissociation covalently-modified layer is used as the substrate, the reactive group on its surface is one of an aliphatic carboxyl group, an aliphatic primary amine group, an aliphatic secondary amine group and a thiol reactive group. The thiol reactive group contains a small-size leaving group which can be easily and nucleophilically substituted by a thiol group and leaves the surface of the separation medium. Such a small-size leaving group includes a halogen ion, p-toluenesulfonate group and a trifluoroacetate group. When such reactive groups are absent on the surface of the separation medium without the amphoteric dissociation covalently-modified layer, the separation medium can be provided with these reactive groups by appropriate derivatization to be a separation medium substrate. Then the separation medium substrate is converted into the amphoteric dissociation ion exchange separation medium by modification with an amphoteric dissociation group precursor. Cellulose or hydrophilic macroporous resin with hydroxyl groups on the surface as a separation medium can be modified/derived with succinic anhydride or chloroacetic anhydride to obtain the desired reactive group, so that the modified cellulose or macroporous resin is suitable as a substrate for further formation of the amphoteric dissociation covalently-modified layer.

When the separation medium without the amphoteric dissociation covalently-modified layer is used as the substrate and an aliphatic primary amine group and/or an aliphatic secondary amine group are/is provided on the surface as reactive groups for covalent linking, the amine group reacts with a halogenated acetic anhydride or a haloacetic acid active ester and then reacts with a thiol-containing amphoteric dissociation group precursor, or substitutes the halogen in bromacetic acid or iodoacetic acid to form glycine, or reacts with succinic anhydride or a mixture of succinic anhydride and acetic anhydride in the case that the total molar amount of the acid anhydride is not excessive, to form a covalently-modified layer composed of an amphoteric dissociation group.

In this embodiment, the number of positive charges on the surface of the amphoteric dissociation ion exchange separation medium is not less than 90% of the maximum value at pH 3, and the number of negative charges on the surface of the amphoteric dissociation ion exchange separation medium is not less than 90% of the maximum value at pH 11.

The adsorption and elution of a target substance are performed with an ion exchange separation medium by adjusting pH, where the surface of this ion exchange medium is required to be an amphoteric dissociation modification layer, which is significantly different from the surface structure of the classical ion exchange medium. The separation performance of the separation medium can only be maximized in the case that the number of positive charges and the number of negative charges on the surface of the ion exchange separation medium are close to their maximum values respectively at two boundaries of the pH range which both the target substance and the separation medium can tolerate. When the number of the net charges on the surface of the ion exchange separation medium is not less than 90% of the maximum value, the separation performance can be approximately maximized. The hydrophilic group is suitable for the preparation of the amphoteric dissociation ion exchange separation medium, while the aromatic substance is unsuitable as an amphoteric dissociation group precursor. Common groups which ionize to generate negative charges include a phosphomonoester, a phosphodiester, an organic sulfonic acid and an aliphatic carboxylic acid, where the phosphomonoester, the phosphodiester and the organic sulfonic acid all have pKs less than 1.7; and for the carboxylic acid with an isolated carboxyl group, such as acetic acid, the pK of its carboxyl group is near 4.8. In addition, imidazole is hydrophilic and has a pK near 6.0; an isolated primary amine with hydrophilic substituents, such as tris (hydroxymethyl) aminomethane, has a pK near 8.0; methylamine and dimethylamine have a pK near 10.7 and the pK of trimethylamine is near 10.0; and ethylamine, diethylamine and triethylamine all have pKs near 11.0. In another aspect, the spatial neighboring dissociable groups in the amphoteric dissociation modification layer have a significant effect on the respective dissociation constants. For example, the pK of acetic acid is near 4.8 and the pK of ethylamine is near 11.0; tris (hydroxymethyl) aminomethane comprises a neural group adjacent to the amine group and its pK is near 8.0, which is much lower than the pK of ethylamine (11.0); and glycine and alanine both contain equimolar amounts of adjacent aliphatic carboxy group and primary amine group, with the pK near 6.0 and much lower than the mean value (7.8) of the pK of ethylamine and the pK of acetic acid. In addition, there is a great difference in pKs of the carboxyl groups in EDTA or EGTA, and a great difference is also observed between the pKs of the two amine groups in ethylenediamine. If the spatial distribution of the group which dissociates to generate positive charge and the group which dissociates to generate negative charge is random in the amphoteric dissociation covalently-modified layer, the pK of each of the two types of dissociable groups is significantly lower than that of the isolated corresponding group. If the group which dissociates to generate positive charge or the group which dissociates to generate negative charge is clustered and agglomerated, an apparent pK resulting from its full ionization will be higher. The group which dissociates to generate positive charges has a dissociation degree lower than 10% at a pH 1.0 unit higher than pK, and the group which dissociates to generate negative charges both has a dissociation degree lower than 10% at a pH 1.0 unit lower than pK. A common and simplest method for preparing the amphoteric dissociation ion exchange separation medium of the application is to use a group dissociating to generate negative charge which has an ionization degree as far as possible lower than 10% at pH 4.0, and a group dissociating to generate positive charge which has an ionization degree as far as possible lower than 10% at pH 10.0, thus, the separation performance of the separation medium can be maximized between pH 3.0 and pH 11.0. In view of this, the pK of the group dissociating to generate positive charge is required to be as far as possible greater than 4.0, and only an aliphatic carboxylic acid with a plurality of spatially adjacent carboxyl groups can provide a higher apparent pK due to the full ionization of its carboxyl groups; the pK of the group dissociating to generate negative charges is required to be as far as possible lower than 9.0, and only an imidazole group and an aliphatic primary amine group having spatially adjacent substituents which dissociate to generate negative charges or are neutral and hydrophilic can meet the requirements, and the aliphatic primary amine group is required to be separated as far as possible by the aliphatic carboxyl group to reduce its pK. The secondary and tertiary amines substituted with an ethyl or a larger alkyl have higher pK and strong hydrophobicity, so that they are not suitable for the preparation of the separation medium. Even if a methyl-substituted aliphatic secondary or tertiary amine is used to adjust the pIm, the molar ratio of which to the total of aliphatic primary amine and imidazole should be as low as possible. Theoretically, the separation performance of the separation medium having a covalently-modified layer composed of the above amphoteric dissociation groups on the surface can be maximized at a pH between 3.0 and 11.0.

Obviously, the molar ratio of the group dissociating to generate negative charge to the group dissociating to generate positive charge not only determines the proportion of the positively charged aliphatic primary amine/imidazole group relative to the nearly fully-ionized aliphatic carboxyl group at pH 11.0, but also determines the proportion of the negatively charged aliphatic carboxyl group relative to the nearly fully-ionized aliphatic primary amine/imidazole group at pH 3.0, that is, the maximum separation performance depends on whether the net charge on the surface of the separation medium is nearly maximized at the boundaries of this pH range. It is apparent that a ratio between the two types of dissociable groups on the surface of the amphoteric dissociation separation medium of the invention is required to be optimized. At a pH 3 units lower than the pK of an acidic dissociable group or 3 units greater than the pK of a basic dissociable group, the dissociation/ionization degree of the acidic or basic dissociable group is lower than 0.1%. It is reasonable to assume that the difference between the pK of the adjacent aliphatic carboxyl group and aliphatic primary amine group is still much greater than 2.5. When at a pH 1 unit higher than the pK of the above group dissociating to generate positive charges, the dissociation degree of the aliphatic carboxyl group to generate negative charges may exceed 99% and the ionization degree of the group dissociating to generate positive charge is lower than 10%. When at a pH 1 unit lower than the pK of the group dissociating to generate negative charges, the dissociation degree of the aliphatic carboxyl group to generate negative charges is lower than 10% and the dissociation degree of the above group dissociating to generate positive charges may exceed 99%. It is assumed that an ionization degree of the aliphatic carboxyl group on the surface of the amphoteric dissociation separation medium of the present invention to dissociate to generate a negatively charged group is lower than 2% at pH 3.0 due to the apparent pK near 4.8. At pH 11.0, the ionization degree of the aliphatic carboxyl group to dissociate to generate a positively charged group is lower than 1% since the pK of the primary amine with a hydrophilic aliphatic substituent is less than 9.0 and contents of the aliphatic secondary and tertiary amines are negligible, and in such case, as long as the molar ratio of the aliphatic carboxyl group to the total of the aliphatic primary amine group and the imidazolyl group is 1:6 to 3:1, the separation performance may be nearly maximized between pH 3.0 and pH 11.0. Given that a higher density of the surface aliphatic carboxyl group may allow more carboxyl groups to be adjacent so that the pK of the carboxyl group may be increased and the adjacency between the carboxyl group and the amine group may lower the pK of the amine group, the present invention limits the ratio of the aliphatic primary amine group (the total of the secondary amine and the tertiary amine accounts for not higher than 30% of the group dissociating to generate positive charge) to the aliphatic carboxyl group to 1:6 to 6:1 to enable the maximization of the separation performance at pH 3.0 to 11.0. A mixture of the two types of precursors containing the group dissociating to generate positive charges and the group dissociating to generate negative charges or the well-designed type C precursor can be used to control such ratio in the modification.

In fact, at a pH at which electrostatic attraction is generated, more net charges on the surface of the separation medium lead to a greater adsorption of the target substance. At a pH at which electrostatic repulsion is generated, the adsorbed target substance can be efficiently eluted as long as the net charges on the surface of the separation medium and the net charge on the target substance are the same and have sufficient amounts. Theoretically, when the separation medium without an amphoteric dissociation covalently-modified layer on the surface is used as a substrate for surface modification, the total molar amount of the group dissociating to generate negative charges and the group dissociating to generate positive charges formed on the surface by covalent modification is limited since there is a limitation in the amount or density of the reactive groups on the surface of the medium to be modified. Different molar ratios of the group dissociating to generate negative charges to the group dissociating to generate positive charges may lead to difference in the pIm of the corresponding amphoteric dissociation separation mediums. For different target substances, amphoteric dissociation ion exchange separation mediums with different pIms are required to maximize the separation performance and maximize the yield of target substances. Accordingly, less aliphatic carboxyl group on the surface of the amphoteric dissociation ion exchange separation medium for adsorbing negatively charged target substances is suitable to allow the medium for positive charge with a larger absolute value. Less aliphatic primary amine group or imidazolyl group on the surface of the amphoteric dissociation ion exchange separation medium for adsorbing positively charged target substances is suitable to allow the medium for negative charge with a larger absolute value. Therefore, a wider range of the ratio of the total of the aliphatic primary amine group and the imidazolyl group to the aliphatic carboxyl group results in a wider range of the pIm of the corresponding amphoteric dissociation ion exchange separation medium. It is required that when used for separating negative ions, the amount of positive charges on the surface of the amphoteric dissociation ion exchange separation medium is not lower than 90% of the maximum value at pH 3.0, and when used for separating positive ions, the amount of negative charges on the surface of the amphoteric dissociation ion exchange separation medium is not lower than 90% of the maximum value at pH 11.0.

A general method for preparing the amphoteric dissociation ion exchange separation medium is to use a separation medium having a reactive group but no amphoteric dissociation modification layer on the surface as a substrate to directly or indirectly but covalently link with an amphoteric dissociation group precursor having a corresponding group for covalent linking to produce the desired amphoteric dissociation covalently-modified layer. For the extraction of nucleic acids which are required to be amplified by PCR for detection, it is required that the non-specific adsorption of the amphoteric dissociation ion exchange separation medium to small molecules is sufficiently low to reduce the content of interfering materials which are contained in the extracted nucleic acids and can inhibit the PCR. Polyethylene glycol is a neutral hydrophilic polymer and is also a commonly-used modifier against non-specific protein adsorption. However, polyethylene glycol is actually a surfactant having an extremely high solubility in chloroform and a strong non-specific adsorption to small hydrophobic molecules. Therefore, the separation medium prepared by modification or polymerization with a polyethylene glycol derivative is not suitable as a substrate for preparing the amphoteric dissociation ion exchange medium of the invention, and the carboxyl group derivative and the primary amino group derivative of the polyethylene glycol are also not suitable as the amphoteric dissociation group precursor of the invention. In particular, the polyethylene glycol molecules have a structure of linear straight chain so that the size exclusion between the molecules is strong, which is not conducive to improving the modification degree of the amphoteric dissociation group, generating difficulty in increasing the separation capacity of the obtained amphoteric dissociation separation medium and failing to reduce the non-specific adsorption to small hydrophobic molecules by ensuring the modification degree. In this regard, it is not suitable for extracting nucleic acids and separating proteins with an ion exchange separation medium bearing amphoteric dissociation groups on the surface which prepared from direct polymerization of polyethylene glycol derivatives, or with an ion exchange separation medium bearing amphoteric dissociation groups which is prepared by modification with the polyethylene glycol derivatives. Therefore, the method of the invention for preparing an amphoteric dissociation ion exchange separation medium by covalent modification is not suitable for the preparation of a separation medium substrate with a linear macromolecule polymer but without an amphoteric dissociation group on the surface. A separation medium prepared by polymerization of a linear macromolecule, even if there is an amphoteric dissociation group on the surface at pH 3.0-11.0, does not belong to the amphoteric dissociation ion exchange separation medium of the invention.

Obviously, it is required that a small molecule as the amphoteric dissociation group precursor and a linking reaction with a yield as high as possible at room temperature are employed to generate the high-density amphoteric dissociation modification layer to reduce the non-specific adsorption to small hydrophobic molecules. In order to prepare the high-density modification layer to reduce the non-specific adsorption to hydrophobic substances, the amphoteric dissociation group precursor for modification is required to be controlled to have a molecular weight within 500 Daltons and have no hydrophobic bulky substituents. There is no requirement for anaerobic and anhydrous reaction to perform the amide formation and the substitution with a thiol group so that they are suitable for the linking reactions required for the modification. In the case that the amphoteric dissociation modification layer is formed on the surface of the separation medium without the amphoteric dissociation modification layer which is used as the substrate, the aliphatic carboxyl group, the aliphatic primary and secondary amine groups and the thiol reactive group on the surface of the separation medium substrate to be modified are suitable as reactive groups, and the primary aliphatic amine group or the aliphatic thiol group is correspondingly required on the amphoteric dissociation group precursor as a group for the covalent linking. In general, when the separation medium without an amphoteric dissociation covalently-modified layer is used as the substrate, the reactive group contained on the surface is one of the aliphatic carboxyl group, the aliphatic primary amine group, the aliphatic secondary amine group and the thiol reactive group, where the thiol reactive group contains a small-size leaving group which is nucleophilically substituted by the thiol group easily and leaves the surface of the separation medium. Such a small-size leaving group contains a halogen ion or a p-toluene-sulfonate group. In the case that the reactive group is absent on the surface of the separation medium without the amphoteric dissociation covalently-modified layer, this separation medium can be provided with the above reactive groups by derivatization to be used as the substrate for covalent modification.

Figure 2:
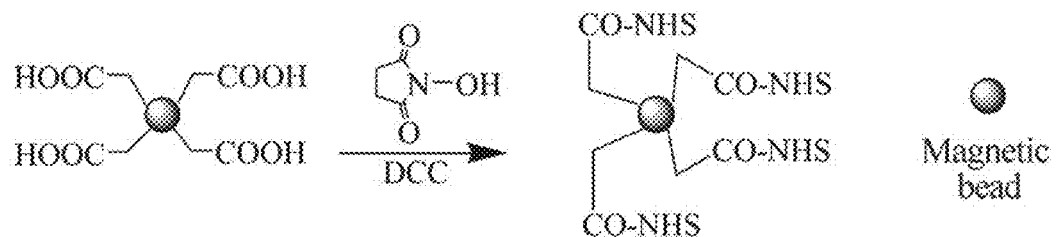
FIG. 2 schematically shows the process of converting FBD-MSP-FCOOH into an active ester.
Figure 3:
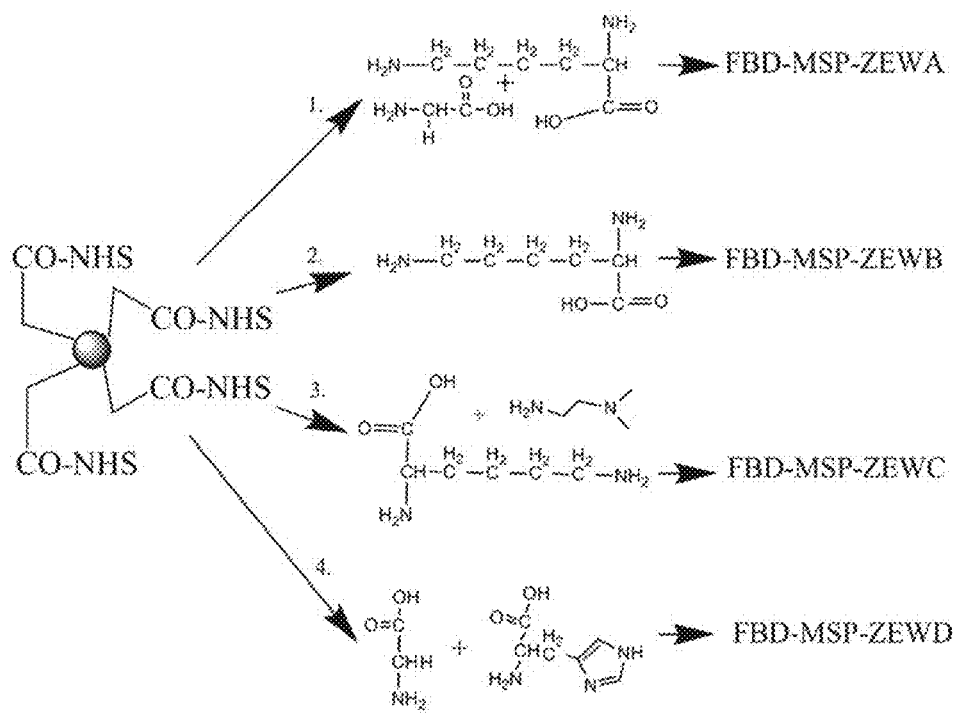
FIG. 3 shows the formation of an amphoteric dissociation covalently-modified layer from an FBD-MSP-FCOOH active ester by forming an amide bond.
Figure 4:
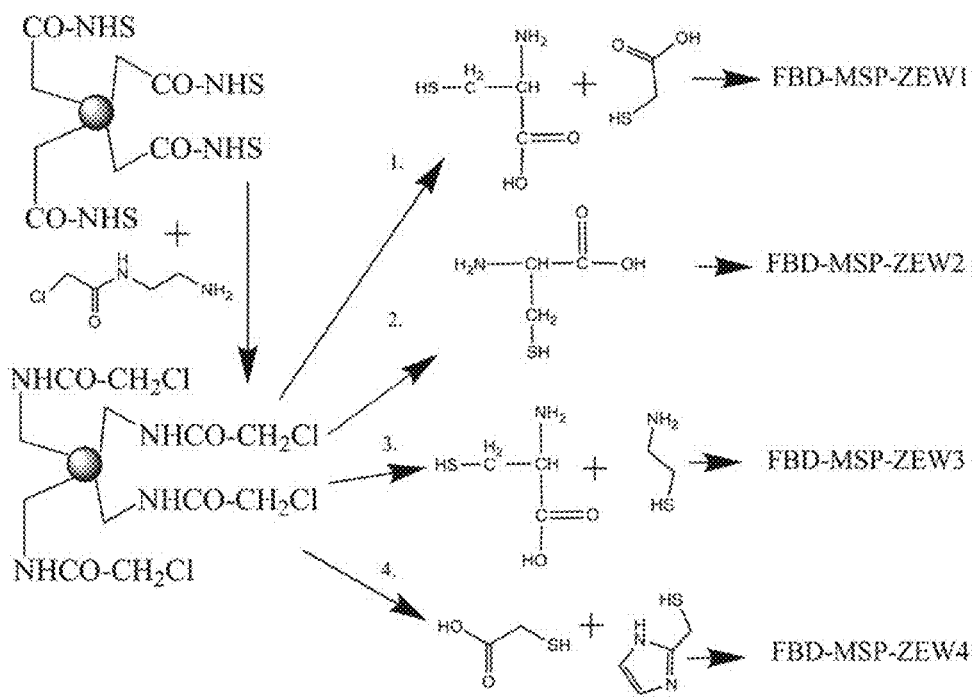
FIG. 4 shows the formation of an amphoteric dissociation covalently-modified layer by converting FBD-MSP-FCOOH active ester into a thiol reactive group.

The technology disclosed in Chinese Patent ZL201610963764.X uses a zwitterion pair of which the surface consists of quaternary amine and sulfonic acid to prepare a separation medium with a hydrophilic surface by modification. By such technology was obtained a product FBD-MSP-FCOOH which is a micro magnetic bead. Besides the aliphatic carboxyl group as a functional group for coupling with other substances, the rest of the surface of the FBD-MSP-FCOOH is a zwitterion pair modification group which consists of quaternary amine and sulfonic acid and has a net charge of zero at pH 2.0-13.0 due to the absence of amphoteric dissociation, leading to a low non-specific adsorption of the surface to hydrophobic substances and proteins. Therefore, FBD-MSP-FCOOH is the desired separation medium substrate without the amphoteric dissociation modification layer for preparing the amphoteric dissociation ion exchange separation medium of the invention. Accordingly, the aliphatic carboxyl group on the surface of this separation medium is activated (as shown in FIG. 2) and further derivatized to prepare a series of amphoteric dissociation ion exchange micro magnetic beads with different pIms (as shown in FIGS. 3 and 4). These ion exchange separation mediums can adsorb nucleic acids at a weakly acidic pH based on the electrostatic attraction of the surface positive charge to the target substance, and the adsorbed nucleic acids can be efficiently released at a weakly basic pH based on electrostatic repulsion; or these ion exchange separation mediums can adsorb basic proteins at an appropriate neutral pH and a meta-alkalescent pH and the adsorbed proteins can be released under weakly acidic or strongly basic conditions, which is a more suitable ion exchange method for purifying the proteins of poor solubility. This novel ion exchange separation medium provides higher selectivity to nucleic acids, and has a separation capacity exceeding 10 times that of the DynabeadsMyone Silane (silanol magnetic beads, Thermo-Fisher Corporation), resulting in less interfering impurities in the extracted nucleic acid. Therefore, when used as a PCR template, the nucleic acid extracted by such separation medium involves higher potency compared to that extracted by the silanol magnetic beads. These micro magnetic beads are also suitable for the rapid purification of the *Pichiaguilliermondii* uricase which has a pK near 9.0 and has a poor solubility at a neutral pH, and the elution yield is near 80% with reference to the enzymatic activity assay, to which the elution yield of the classical cation exchanger is far from satisfaction. However, when the amphoteric dissociation ion exchange separation medium is used to separate proteins, the saturated adsorption of proteins may hinder the response of the dissociation state of the dissociation group on the surface of the separation medium to the eluent pH, so that more eluent is required to elute the medium in batches to ensure the elution efficacy.

In addition, the separation capacity is required to be accurately calibrated in the production process of the amphoteric dissociation ion exchange separation medium for controlling the product quality. Calibrating the separation capacity of these ion exchange separation mediums for nucleic acids as the target substance is the prerequisite to ensure the reproducibility of test when the nucleic acids are used for high sensitivity analysis after extraction and concentration with such mediums. In order to determine the property of the amphoteric dissociation ion exchange separation medium of the invention, that is, its pIm, a simple method is required to determine variations of the separation capacity and the elution efficacy for the charged target substance with the adsorption pH. Quantitatively determining nucleic acids obtained by adsorption and separation with this product is the most direct method to calibrate the adsorption and separation capacity of this product. Fluorescence quantitative PCR, i.e., qPCR, is required for the quantification of nucleic acids, where the minimum number of cycles for the determination to reach the set signal is inversely proportional to the logarithm of the template nucleic acid amount. However, this quantitative method involves low determination accuracy, high cost and time-consuming analysis, unsuitable for the quality control during the production process and inconvenient for the characterization of the properties, such as pIm, of the novel ion exchange separation medium of the invention. The spectrophotometric assay involves simple and rapid determination and good reproducibility, and measurement of the absorbance is easy to be standardized, suitable for the calibration and tracing of the product quality and for the characterization of the amphoteric dissociation property of the amphoteric dissociation ion exchange separation medium of the invention. Though nucleic acids have strong ultraviolet absorbance, impurities introduced in the adsorption and elution of nucleic acids may interfere with the measurement of ultraviolet absorbance. In addition, nucleic acids as the probe involve high cost and poor stability. A stable charged colored small molecule organic material which is easy to be quantified by spectrophotometry can act as a color-developing probe, which is suitable for rapidly and easily calibrating the separation capacity of the ion exchange separation medium and characterizing its pIm property. The application employs a water-soluble aromatic organic substance which has strong visible light absorbance and easy dissociation as the color-developing probe, enabling efficient adsorption and elution of the probe at room temperature by adjusting pH and rapidly and accurately calibrating the adsorption and separation capacity of the ion exchange separation medium based on the strong visible light absorbance of the probe in the eluent. Moreover, the probe can be used for controlling the product quality and characterizing the pIm of the amphoteric dissociation ion exchange separation medium of the invention (as shown in FIG. 1), thereby determining the special amphoteric dissociation property and elution efficacy of the amphoteric dissociation ion exchange separation medium.

The application further discloses a use method of the amphoteric dissociation ion exchange separation medium, comprising: applying the amphoteric dissociation ion exchange separation medium to adsorb and separate a target substance; wherein a common logarithm of a dissociation constant obtained from the release of hydrogen ion from the target substance is pK or an isoelectric point of the target substance is pIs; and the method further comprises:

a. selecting an amphoteric dissociation ion exchange separation medium; wherein the difference between the pIm of the amphoteric dissociation ion exchange separation medium and the pK of the target substance is not less than 1.0;

b. adsorbing the target substance; wherein an environment pH is selected to allow the type of net charge on the surface of the ion exchange separation medium to be opposite to the type of net charge of the target substance, thereby resulting in adsorption of the target substance by electrostatic attraction, wherein the environmental pH is located between the pK of the target substance and the pIm of the amphoteric dissociation ion exchange separation medium while the difference between the environmental pH and the pK of the target substance and the difference between the environmental pH and the pIm of the amphoteric dissociation ion exchange separation medium are both greater than 0.3; and c. eluting the target substance; wherein when pH of an eluent is lower than the pIm of the amphoteric dissociation ion exchange separation medium, the pH of the an eluent is at least 0.3 lower than the lower one of the pK of the target substance and the pIm of the amphoteric dissociation ion exchange separation medium; when the pH of the eluent is higher than the pIm of the amphoteric dissociation ion exchange separation medium, the pH of the an eluent is at least 0.3 higher than the higher one of the pK of the target substance and the pIm of the amphoteric dissociation ion exchange separation medium; in the use of the above eluent, the type of net charges on the surface of the amphoteric dissociation ion exchange separation medium is the same as that on the target substance, thereby resulting in elution of the target substance by electrostatic repulsion; and a water-soluble monovalent neutral inorganic salt is added to the eluent to promote the elution of the target substance.

The application also discloses a method for calibrating separation capacity of the amphoteric dissociation ion exchange separation medium, comprising:

a) selecting an colored organic compound as a color-developing probe for the calibration of the separation capacity of the amphoteric dissociation ion exchange separation medium; wherein the colored organic compound has a dissociation constant or an isoelectric point of pKa, a molecular weight less than 600 Daltons, a visible light absorption coefficient greater than 14 $mM^{-1}$ $cm^{-1}$, a solubility not less than 5.0 µmol/L at pH 3.0-11.0, and a positive or negative net charge after dissociation at pH 3.0-11.0;

b) calibrating the separation capacity of the amphoteric dissociation ion exchange separation medium; wherein step b comprises:

b1) when the amphoteric dissociation ion exchange separation medium has an isoelectric point pIm between 4.0 and 6.0, using a cationic probe with a dissociation constant pK or an isoelectric point pI at least 2.0 greater than the pIm of the amphoteric dissociation ion exchange separation medium, or using an anionic probe with a dissociation constant pK or an isoelectric point pI at least 2.0 lower than the pIm of the amphoteric dissociation ion exchange separation medium; and b2) when the amphoteric dissociation ion exchange separation medium has the pIm between 6.0 and 10.0, using the anionic probe with a dissociation constant or an isoelectric point pKa at least 2.0 lower than the pIm of the amphoteric dissociation ion exchange separation medium;

c) when calibrating the separation capacity of the amphoteric dissociation ion exchange separation medium, selecting a buffer solution corresponding to an environmental pH to allow the amphoteric dissociation ion exchange separation medium to adsorb a color-developing probe by electrostatic attraction, wherein the environmental pH is between the dissociation constant pK or the isoelectric point pI of the color-developing probe and the pIm of the amphoteric dissociation ion exchange separation medium, and differs from the pIm of the amphoteric dissociation ion exchange separation medium by not less than 1.3 and differs from the dissociation constant pK or the isoelectric point pI of the color-developing probe by not less than 0.5; selecting a buffer solution corresponding to an environmental pH to allow the type of net charges on the surface of the amphoteric dissociation ion exchange separation medium to be the same as that of the color-developing probe in the elution, thereby eluting a color-developing probe by electrostatic repulsion, wherein the environmental pH is at least 1.3 higher than the higher one or at least 1.3 lower than the lower one of the dissociation constant pK or the isoelectric point pI of the color-developing probe and the pIm of the amphoteric dissociation ion exchange separation medium; measuring the absorbance of the color-developing probe in an eluate followed by conversion into a separation capacity for the color-developing probe; and determining the effect of pH on the separation capacity of the amphoteric dissociation ion exchange separation medium for a color-developing probe; wherein the minimum pH at which the separation capacity for the color-developing probe with negative net charge reaches zero after the dissociation, or the maximum pH at which the separation capacity for the color-developing probe with positive net charge reaches zero after the dissociation, is an approximation of the pIm of the amphoteric dissociation ion exchange separation medium.

That is, the variation of the separation capacity of the amphoteric dissociation ion exchange separation medium for the color-developing probe with pH is determined, where the minimum pH at which the separation capacity for the color-developing probe dissociating to generate negative ions reaches zero, or the maximum pH at which the separation capacity for the color-developing probe dissociating to generate positive ions reaches zero, is its pIm.

The amount of the adsorbed color-developing probe can be estimated by determining the amount of the remaining color-developing probe after the adsorption. Effect of the pH of the eluent on the elution efficacy can be compared by determining the amount of the color-developing probe in the eluate, thereby determining the efficacy of eluting the charged substance based on the electrostatic repulsion of the invention.

There are fewer quaternary amine-type cationic color-developing probes but many sulfonic acid-type anionic color-developing probes. Acid red 13 as an anionic dye is a representative color-developing probe to characterize the separation capacity of the amphoteric dissociation ion exchange separation medium and determine the pIm.

Described below are the embodiments, and reagents and materials used in the embodiments are listed as follows.

Silanol micro magnetic beads: DynabeadsMyone Silane (silanol magnetic beads) (Cat. no. 37002D), purchased from Thermo Fisher Scientific Corporation.

Magnetic separation rack: 8-hole magnetic separation rack, provided by BioCanal Scientific Inc. (Wuxi, Jiangsu).

Conventional PCR instrument: BioradT100thermal cycler.

Fluorescence real-time quantitative PCR instrument: BioradCFXConnect.

Carboxyl magnetic beads FBD-MSP-FCOOH: the carboxyl magnetic beads FBD-MSP-FCOOH, prepared according to Chinese Patent ZL201610963764.X and neutral at pH 2.0-12.0 due to the modification layer of ion pairs consisting of quaternary amine and sulfonic acid on the surface.

Pichia guilliermondiiuricase RMGU expression plasmid: see Genbank for sequence with the Accession No. KY706244; isoelectric point 8.9; the fully synthetic coding sequence is ligated to an expression vector pDE1 to obtain a tag-free expression plasmid which together with its protein is called RMGU.

Acid red 13 stock solution: dissolved to 200 mM by distilled water, filtered by 0.22 m microporous membrane, stored at 4° C. and diluted before use.

Nucleic acid adsorption buffer: consisting of an acetic acid-sodium acetate buffer (0.20 M) at pH 3.6-5.8, MES (20 mM) at pH 6.0-6.8 and HEPES (20 mM) at pH 7.0-8.0; unless otherwise specified, a nucleic acid adsorption buffer at pH 3.6 is employed.

Nucleic acid elution buffer: Tris-HCl (25 mM) at pH 8.0-9.0; unless otherwise specified, a nucleic acid elution buffer at pH 8.9 is employed.

Magnetic bead washing buffer: an acetic acid-sodium acetate buffer (0.20 M) at pH 3.6.

Nucleic acid quantification: unless otherwise specified, the quantification is performed by measuring the absorbance at 260 nm using Nanodrop.

Nucleic acid electrophoresis: premixed ethidium bromide-agarose gel electrophoresis recorded by a nucleic acid-protein imager with a detection limit of about 80 ng.

Uricase activity detection solution: consisting of borax (0.20M, pH 9.2) and uric acid (0.10 mM); consumption of 1.0 μmol of substrate per minute refers to 1 unit.

Cell Lysis Solution 1: HEPES (20 mM, pH 7.6), for lysing recombinant RMGU-expressing *E. coli* cells.

Protein eluent 1:glycine-sodium hydroxide buffer (pH 10.0).

Protein electrophoresis: conventional SDS-PAGE; unless otherwise specified, 5 g of the total protein for loading.

Protein concentration determination: using Bradford's dye binding method or measuring the absorbance at 280 nm with Nanodrop.

The required chemical reagents are purchased from Tansoole and Aladdin reagent website with purity above 95%.

Described below are examples of the invention.

Example 1 Preparation of an Amphoteric Dissociation Ion Exchange Separation Medium with a Representative Structure Step 1 Preparation of the following solutions (performing the filtration with 0.22 m filtration membrane for simultaneous sterilization)

1) Lysine solution: prepared by adjusting a lysine solution (100 mM) to pH 6.0 with hydrochloric acid (50 mM) and diluting the resulting solution to 30 mM with water followed by filtration for use.

2) Histidine solution: prepared by adjusting a histidine solution (50 mM) to pH 6.0 with hydrochloric acid (10 mM) and diluting the resulting solution to 30 mM.

3) Glycine solution: prepared by adjusting a glycine solution (100 mM) to pH 6.0 with dilute sodium bicarbonate and diluting the resulting solution to 30 mM with water followed by filtration for use.

4) N,N-dimethylethylenediamine solution: prepared by adjusting a N,N-dimethylethylenediamine solution (10 mM) to pH 6.0 with hydrochloric acid (0.10 M) and diluting the resulting solution to 10 mM.

5) Cysteine solution: prepared by adjusting an aqueous cysteine solution (50 mM) to pH 6.0 with sodium bicarbonate (10 mM) and diluting the resulting solution to 10 mM followed by filtration for use (required to be used within 30 minutes after the preparation).

6) Mercaptoethylamine solution: prepared by adjusting an aqueous mercaptoethylamine solution (20 mM) to pH 6.0 with hydrochloric acid (10 mM) and diluting the resulting solution to 10 mM (required to be used within 30 minutes after the preparation).

7) Thioglycolic acid solution: prepared by adjusting an aqueous thioglycolic acid solution (20 mM) to pH 6.0 with sodium bicarbonate (10 mM) and diluting the resulting solution to 10 mM (required to be used within 30 minutes after the preparation).

8) 2-mercaptoimidazole solution: prepared by adjusting a 2-mercaptoimidazole solution (20 mM) to pH 6.0 with sodium bicarbonate (10 mM) and diluting the resulting solution to 10 mM (required to be used within 30 minutes after the preparation).

Step 2 Activation of the carboxyl group of FBD-MSP-FCOOH into an active ester

FBD-MSP-FCOOH was repeatedly washed with a dry N,N-dimethylformamide (DMF), and then suspended with the dry DMF to produce a suspension of 10 g/L. The suspension was added with dicyclohexylcarbodiimide (DCC) having a weight 3 times that of the FBD-MSP-FCOOH and N-hydroxysuccinimide (NHS—OH) having a weight 1.5 times that of the FBD-MSP-FCOOH. The reaction mixture was mixed uniformly and reacted continuously at 28-35° C. for 12 hours. The activated magnetic beads were washed three times with DMF to give an NHS active ester of the FBD-MSP-FCOOH magnetic bead, abbreviated as FBD-MSP-FCONHS (as shown in FIG. 2), where in each of the washing, a mass-to-volume ratio of the FBD-MSP-FCOOH to the DMF is 1 (g):100 (mL).

Step 3 Covalent modification of an active ester by formation of an amide to produce an amphoteric dissociation ion exchange separation medium (as shown in FIG. 3)

(1) FBD-MSP-FCONHS was suspended in a mixture prepared by the lysine solution and the glycine solution in a volume ratio of 7:3 to produce a modification system for modification, where a mass-to-volume ratio of the FBD-MSP-FCONHS to the mixture is 1 (g):100 (mL). The modification system was reacted under medium-speed stirring at room temperature for 13 hours. The resulting magnetic beads were washed three times with distilled water in a mass-to-volume ratio of 1 (g):100 (mL) to give corresponding amphoteric dissociation ion exchange micro-magnetic beads, abbreviated as FBD-MSP-ZEWA.

(2) FBD-MSP-FCONHS was suspended in the lysine solution in a mass-to-volume ratio of 1 (g):100 (mL) to produce a modification system for modification. The modification system was reacted under medium-speed stirring at room temperature for 13 hours. The resulting magnetic beads were washed three times with distilled water in a mass-to-volume ratio of 1 (g):100 (mL) to give corresponding amphoteric dissociation ion exchange micro-magnetic beads, abbreviated as FBD-MSP-ZEWB.

(3) FBD-MSP-FCONHS was suspended in a mixture prepared by the lysine solution and the N,N-dimethylethylenediamine solution in a volume ratio of 7:3 to produce a modification system for covalent modification, where a mass-to-volume ratio of the FBD-MSP-FCONHS to the mixture is 1 (g):100 (mL). The modification system was reacted under medium-speed stirring at room temperature for 13 hours. The resulting magnetic beads were washed three times with distilled water in a mass-to-volume ratio of 1 (g):100 (mL) to give corresponding amphoteric dissociation ion exchange micro-magnetic beads, abbreviated as FBD-MSP-ZEWC.

(4) FBD-MSP-FCONHS was suspended in the histidine solution in a mass-to-volume ratio of 1 (g):100 (mL) to produce a modification system for covalent modification. The modification system was reacted under medium-speed stirring at room temperature for 13 hours. The resulting magnetic beads were washed three times with distilled water in a mass-to-volume ratio of 1 (g):100 (mL) to give corresponding amphoteric dissociation ion exchange micro-magnetic beads, abbreviated as FBD-MSP-ZEWD.

(5) FBD-MSP-FCONHS was suspended in the N,N-dimethylethylenediamine solution in a mass-to-volume ratio of 1 (g):100 (mL) to produce a modification system for covalent modification. The modification system was reacted under medium-speed stirring at room temperature for 13 hours. The resulting magnetic beads were washed three times with distilled water in a mass-to-volume ratio of 1 (g):100 (mL) to give corresponding amphoteric dissociation ion exchange micro-magnetic beads, abbreviated as FBD-MSP-ZEWE.

Step 4 Linking to a thiol reactive group for covalent modification to produce an amphoteric dissociation ion exchange separation medium (as shown in FIG. 4)

(1) FBD-MSP-FCONHS was suspended in dimethylformamide in a mass-to-volume ratio of 1 (g):100 (mL) to produce a suspension. The suspension was added with monochloroacetoethylenediamine (0.5 g) and reacted at room temperature under shaking for 4 hours to give a separation medium to be modified which has a chloroacetyl group as a thiol reactive group and is abbreviated as FBD-MSP-FCOCH$_2$Cl.

(2) FBD-MSP-FCOCH$_2$Cl was suspended in a mixture prepared by the cysteine solution and the thioglycolic acid solution in a volume ratio of 7:3 to produce a modification system for modification, where a mass-to-volume ratio of the FBD-MSP-FCOCH$_2$Cl to the mixture is 1 (g):100 (mL). The modification system was reacted under medium-speed stirring at room temperature for 13 hours. The resulting magnetic beads were washed three times with distilled water in a mass-to-volume ratio of 1 (g):100 (mL) to give corresponding amphoteric dissociation ion exchange micro-magnetic beads, abbreviated as FBD-MSP-ZEW1.

(3) FBD-MSP-FCOCH$_2$Cl was suspended in the cysteine solution in a mass-to-volume ratio of 1 (g):100 (mL) to produce a modification system for covalent modification. The modification system was reacted under medium-speed stirring at room temperature for 13 hours. The resulting magnetic beads were washed three times with distilled water in a mass-to-volume ratio of 1 (g):100 (mL) to give corresponding amphoteric dissociation ion exchange micro-magnetic beads, abbreviated as FBD-MSP-ZEW2.

(4) FBD-MSP-FCOCH$_2$Cl was suspended in a mixture prepared by the cysteine solution and the mercaptoethylamine solution in a volume ratio of 7:3 to produce a modification system for covalent modification, where a mass-to-volume ratio of the FBD-MSP-FCOCH$_2$Cl to the mixture is 1 (g):100 (mL). The modification system was reacted under medium-speed stirring at room temperature for 13 hours. The resulting magnetic beads were washed three times with distilled water in a mass-to-volume ratio of 1 (g):100 (mL) to give corresponding amphoteric dissociation ion exchange micro-magnetic beads, abbreviated as FBD-MSP-ZEW3.

(5) FBD-MSP-FCOCH$_2$Cl was suspended in a mixture prepared by the thioglycolic acid solution and the 2-mercaptoimidazole solution in a volume ratio of 1:1 to produce a modification system for covalent modification, where a mass-to-volume ratio of FBD-MSP-FCOCH$_2$Cl to the mixture is 1 (g):100 (mL). The modification system was reacted under medium-speed stirring at room temperature for 13 hours. The resulting magnetic beads were washed three times with distilled water in a mass-to-volume ratio of 1 (g):100 (mL) to give corresponding amphoteric dissociation ion exchange micro-magnetic beads, abbreviated as FBD-MSP-ZEW4.

(6) FBD-MSP-FCOCH$_2$Cl was suspended in the mercaptoethylamine solution to produce a modification system for covalent modification. The modification system was reacted under medium-speed stirring at room temperature for 13 hours. The resulting magnetic beads were washed three times with distilled water in a mass-to-volume ratio of 1 (g):100 (mL) to give corresponding amphoteric dissociation ion exchange micro-magnetic beads, abbreviated as FBD-MSP-ZEW5.

Certainly, the products prepared in the examples are merely illustrative of how to prepare the amphoteric dissociation ion exchange separation medium. The object of the invention can also be achieved by replacing the material with one or more of the other above-described aliphatic carboxyl groups dissociating to generate negative charge, primary, secondary and tertiary amine groups dissociating to generate positive charge and imidazolyl groups dissociating to generate positive charge.

Example 2 Operation Process of Determination of the Adsorption and Separation Capacity of the Amphoteric Dissociation Ion Exchange Medium for Acid Red 13

Step (1)

Figure 5:
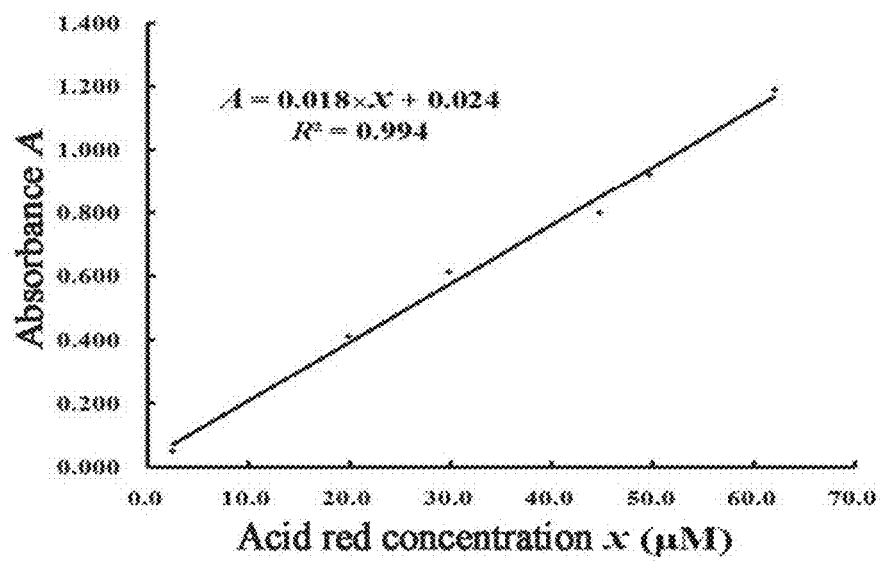
FIG. 5 shows the assay of an extinction coefficient of acid red 13 at pH 8.3.

Effect of pH on the extinction coefficient of the acid red 13 was measured and the results were shown in FIG. 5. No variation was observed in the extinction coefficient of the acid red 13 in a pH range from 4.0 to 8.9, in which the extinction coefficient was maintained at 18.0 $(mM)^{-1} cm^{-1}$. The extinction coefficient of the acid red 13 described below all used this value.

Step (2)

The amphoteric dissociation ion exchange separation medium was washed three times with a buffer (pH 3.6) and then re-suspended with this buffer to produce a suspension.

Step (3)

The acid red 13 was diluted with an adsorption buffer to not less than 5.0 mM.

Step (4)

The required amount of the ion exchange separation medium suspension was transferred, subjected to the aqueous phase removal and resuspended in 0.8 mL of the adsorption buffer to produce a resuspension. No more than 50 μL of a dilute acid red 13 solution was added to the resuspension to the desired final concentration. The reaction mixture was continuously mildly mixed at room temperature by a four-dimensional mixer for 5-10 minutes.

Step (5)

The acid red 13-binding magnetic beads were magnetically separated, washed twice with 0.80 mL of a washing buffer, resuspended in 0.80 mL of an elution buffer and rotated and shaken by the four-dimensional mixer for 5-10 minutes. The magnetic beads were removed and 0.70 mL of the supernatant was used for measurement of the absorbance at 506 nm.

Step (6)

The maximum pH at which the separation capacity reaches zero was approximately determined according to the change of the separation capacity of the amphoteric dissociation ion exchange separation medium for the acid red 13 with pH, and was used as the pIm of the tested amphoteric dissociation ion exchange separation medium.

Step (7)

The separation capacity for the acid red 13 in an adsorption buffer (pH 3.6) indicated the separation capacity of the amphoteric dissociation ion exchange separation medium, and was used to measure various magnetic beads with an amphoteric dissociation ion exchange group on the surface.

Example 3 Effect of Adsorption and Elution Conditions on the Separation Capacity of the Amphoteric Dissociation Separation Medium (Referring to Example 2 for Operation)

Step (1)

In the case that the pH for adsorption was 3.6 and the concentration of the acid red 13 was 60 μM, the pH effect of the eluent was shown in Table 1.

The change of the pH of the eluent from 8.0 to 8.9 only had a strong effect on the capacity of FDD-MSP-ZEWC and FBD-MSP-ZEW3 for separating the acid red 13, but the capacity did not increase significantly at the pH greater than 8.9. Unless otherwise specified, an eluent with pH 8.9 was used for both the adsorbed acid red 13 and the adsorbed nucleic acid. The amount of the acid red 13 before the adsorption was used as the total amount. Under the washing conditions used, the proportion of the acid red 13 in the washing solution, i.e., the washing loss rat, was less than 20%. The reduction of acid red 13 in the supernatant indicated the total amount of adsorption. Except FBD-MSP-ZEWE and FBD-MSP-ZEW5, the elution rates of the acid red 13 adsorbed by the tested representative amphoteric dissociation ion exchange magnetic beads at pH 8.9 were greater than 95%. As for the FBD-MSP-ZEWE and the FBD-MSP-ZEW5, the elution rates were lower than 2% even at pH 8.9. The above results supported that the surface net charge can be reversed by adjusting the pH to promote the elution of charged substances.

TABLE 1

Effect of the pH of the eluent on the elution rate of acid red 13 adsorbed by two kinds of amphoteric dissociation adsorption separation magnetic beads

| Amphoteric dissociation ion exchange micro-magnetic bead type | Isoelectric point pIm | Eluent pH | | | pH 8.9 elution rate | Separation capacity μmol/g | |
|---|---|---|---|---|---|---|---|
| | | 8.0 | 8.5 | 8.9 | | pH 3.6 | pH 4.5 |
| | | Absorbance of Eluent at 506 nm | | | | | |
| FBD-MSP-ZEWA | ~4.7 | 0.578 | 0.594 | 0.598 | ~98% | ~55 | ~4 |
| FBD-MSP-ZEWB | ~6.7 | 0.832 | 0.845 | 0.849 | ~97% | 104 | 62 |

TABLE 1-continued

Effect of the pH of the eluent on the elution rate of acid red 13 adsorbed by
two kinds of amphoteric dissociation adsorption separation magnetic beads

| Amphoteric dissociation ion exchange micro-magnetic bead type | Isoelectric point pIm | Eluent pH | | | pH 8.9 elution rate | Separation capacity μmol/g | |
|---|---|---|---|---|---|---|---|
| | | 8.0 | 8.5 | 8.9 | | pH 3.6 | pH 4.5 |
| | | Absorbance of Eluent at 506 nm | | | | | |
| FBD-MSP-ZEWC | ~7.7 | 0.701 | 0.760 | 0.786 | ~95% | 102 | 74 |
| FBD-MSP-ZEWD | ~6.3 | 0.688 | 0.694 | 0.697 | ~97% | 82 | 42 |
| FBD-MSP-ZEWE | ~9.4* | 0.003 | 0.006 | 0.005 | <1% | 114* | 98* |
| FBD-MSP-ZEW1 | ~4.3 | 0.556 | 0.561 | 0.563 | ~98% | 54 | ~3 |
| FBD-MSP-ZEW2 | ~6.1 | 0.812 | 0.830 | 0.833 | ~97% | 98 | 60 |
| FBD-MSP-ZEW3 | ~6.8 | 0.656 | 0.678 | 0.682 | ~95% | 108 | 71 |
| FBD-MSP-ZEW4 | ~5.8 | 0.624 | 0.634 | 0.636 | ~97% | 76 | 39 |
| FBD-MSP-ZEW5 | ~9.2* | 0.003 | 0.005 | 0.006 | <3% | 102* | 96* |

*indicated an extremely low elution efficacy at pH 8.9; the separation capacity was estimated based on the reduction of the acid red 13 in the supernatant after the adsorption and then used to estimate its pIm.

Step (2)

Figure 6:
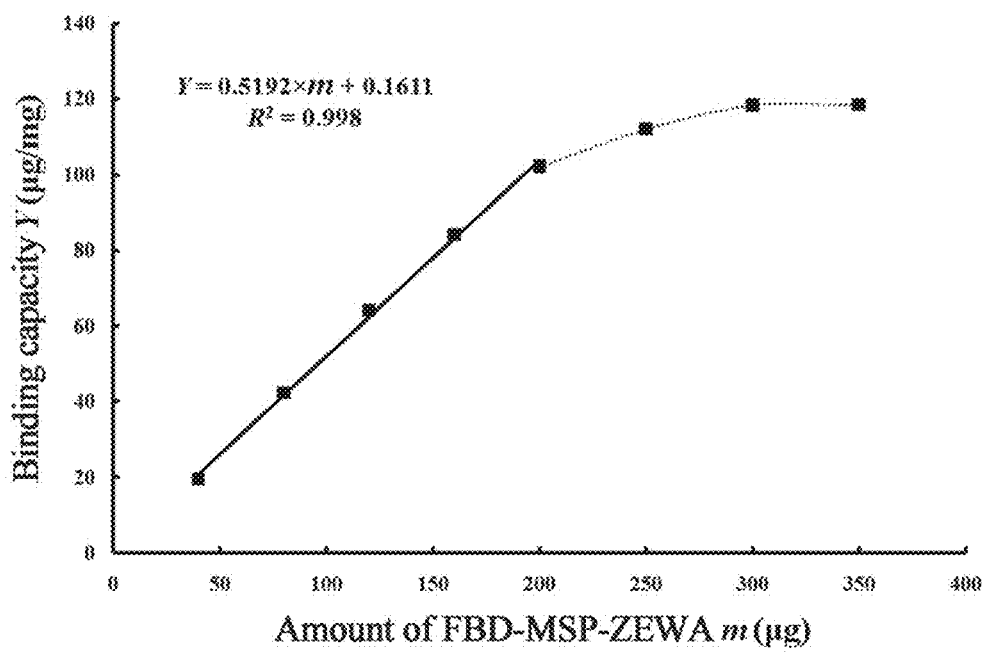
FIG. 6 shows response of the amount of acid red 13 adsorbed and separated to the amount of a reaction system FBD-MSP-ZEWA.
Figure 7:
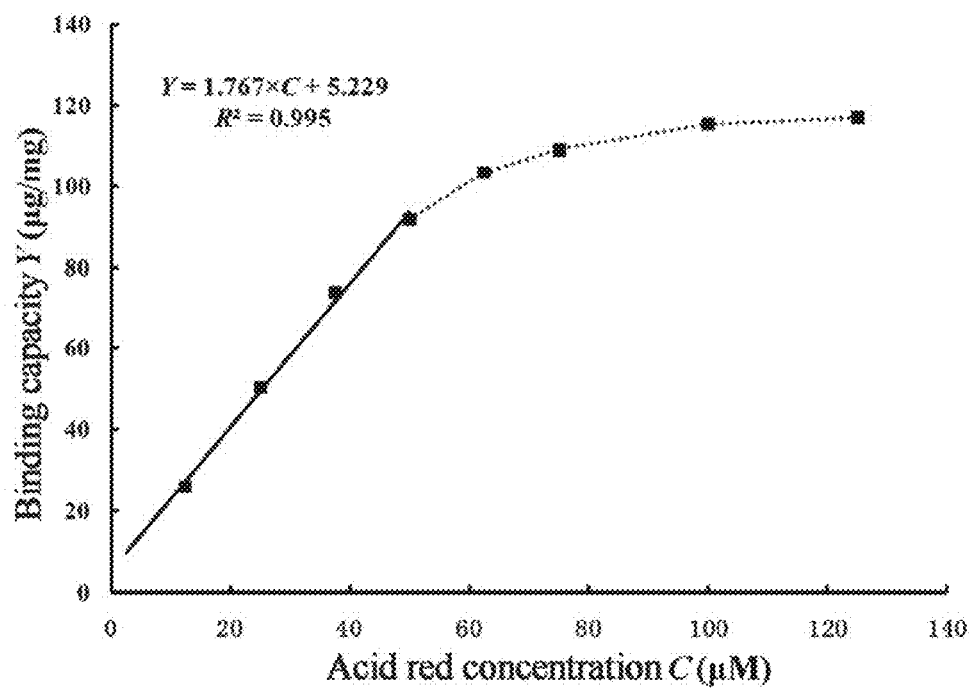
FIG. 7 shows response of the amount of acid red 13 adsorbed and separated to the concentration of a reaction system acid red 13.

In the case that the adsorption and the elution were respectively performed at pH 3.6 and 8.9 and the final concentration of acid red 13 in the adsorption buffer was 60 μM, the relationship between the adsorption separation amount and the effect was determined. The results showed that the amount of acid red 13 obtained in the eluate after separation was in linear response to the amount of FBD-MSP-ZEWB within 160 g (as shown in FIG. 6). Moreover, when different concentrations of acid red 13 were used in the adsorption reaction system in the case of 0.10 mg of FBD-MSP-ZEWA, the amount of acid red 13 in the eluate was in nearly linear response to the amount of acid red 13 in the adsorption reaction system within a limited range (as shown in FIG. 7). Such results indicated that using acid red 13 as a color-developing probe was suitable for the method for calibrating the separation capacity of these amphoteric dissociation separation mediums. In addition, the results also supported that the amphoteric dissociation ion exchanger designed by the invention was suitable for efficiently recycling and reusing the water-soluble dye in the dyeing and weaving waste liquid, thereby facilitating the reuse and reducing environmental pollution.

Figure 8:
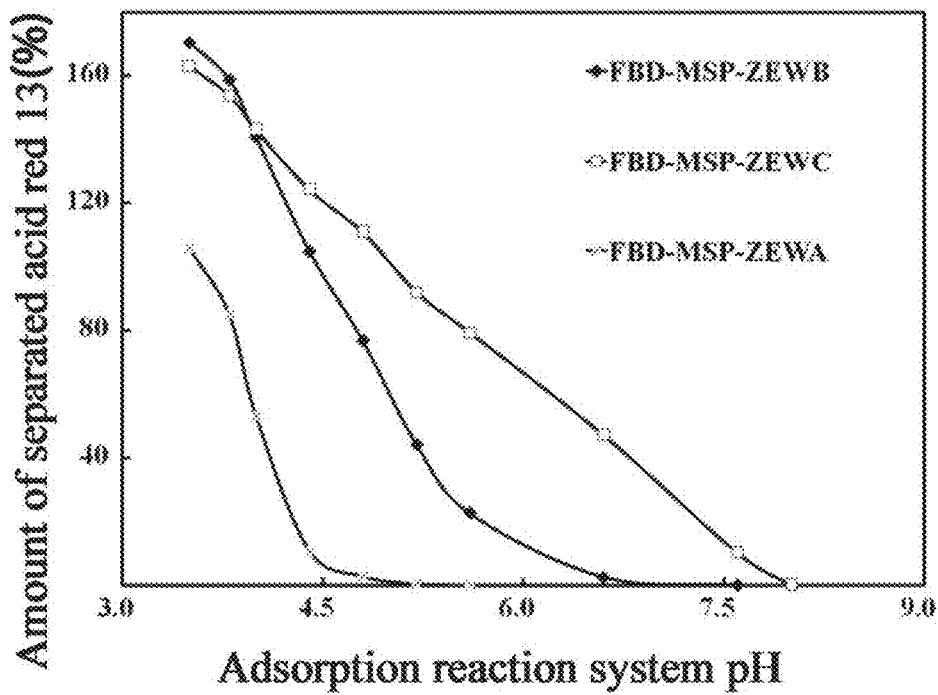
FIG. 8 shows the effect of pH of the adsorption on the capacity of three amphoteric dissociation magnetic beads to separate acid red 13 and the estimation of pIm of the three magnetic beads.

Step (3)

pH of the adsorption reaction also showed significant effect on the separation capacity of the amphoteric dissociation ion exchange separation medium (Table 1), and the representative data was shown in FIG. 8. The separation capacity of the magnetic beads for acid red 13 was reduced at pH of greater than 4.0, indicating the continuous reduction in the positive charge. The pH of the adsorption reaction system should be located between 3.6-4.0 to achieve the maximum separation capacity. The minimum pH at which the separation capacity for acid red 13 was near zero was the pIm, and the pIms of the three exemplary magnetic beads were significantly different (as shown in FIG. 8). At pH 8.0, the adsorption capacities of the three magnetic beads in FIG. 8 for acid red 13 were close to zero, indicating that the net charge on the surface of the three beads was negative. Based on this, the pIm of the prepared amphoteric dissociation ion exchange separation medium can be estimated. In addition, the difference in the pIms also demonstrated the pH effect of the eluent and further supported the design concept of the invention and the application of the resulting ion exchanger (Table 1).

Step (4)

The FBD-MSP-ZEWA (0.10 mg), acid red 13 (60 μM), an adsorption system (0.80 mL, pH 3.6) and an eluent (0.8 mL in total, pH 8.9) were used, and the FBD-MSP-ZEWA was independently diluted. The separation capacity for acid red 13 was repeatedly determined to be (55±2) μmol/g magnetic bead (n=5), which indicated the high precision of this method, suitable for calibrating the separation capacity of the amphoteric dissociation ion exchange separation medium of the invention. The magnetic beads were measured based on the separation amount for acid red 13 at pH 3.6 in the following examples.

Example 4 Application of FBD-MSP-ZEWB and FBD-MSP-ZEWA in the Extraction of Plasmid DNA Step (1)

The RMGU plasmid was used as a model. After E. coli cells underwent scale-up culture, the plasmid was extracted as a nucleic acid sample based on the combination of the base-lysed E. coli cells and the spin column using a spin-column plasmid extraction kit (Tiangen).

Step (2)

Unless otherwise specified, the binding of magnetic beads to a plasmid was all performed at pH 3.6 and the elution was performed at pH 8.9.

Step (3)

Figure 9:
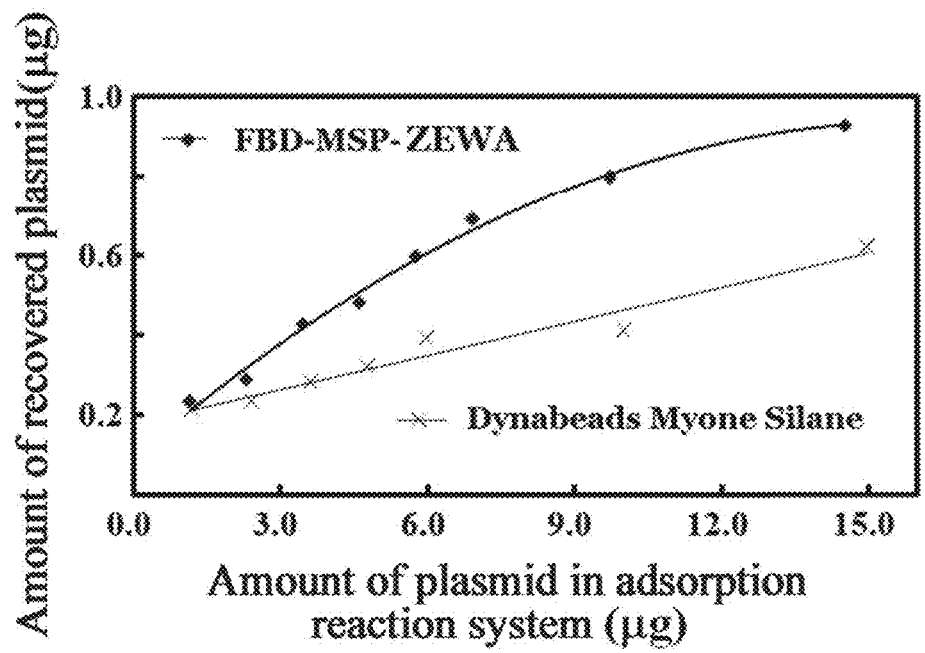
FIG. 9 shows the effect of the amount of plasmid in the adsorption system on the amount of plasmid obtained by magnetic bead separation.

Silanol magnetic beads (0.40 mg, Thermo-Fisher Corporation), FBD-MSP-ZEWA (5.5 nmol, 0.10 mg), an adsorption system (0.20 mL in total) and an eluent (40 μL) were used and nanodrop was employed to determine the amount of nucleic acid through the measurement of A260. The response curve of the nucleic acid amount obtained from the separation to the excess nucleic acid amount in the adsorption reaction system was shown in FIG. 9. It can be seen that in the case of excess nucleic acid, the capacity of the FBD-MSP-ZEWA for separating nucleic acids was significantly higher than 4 times that of the silanol magnetic bead (Thermo-Fisher Corporation). The maximum amount of nucleic acid adsorbed by the magnetic beads is obtained by subtracting the amount of nucleic acid remained in the supernatant after adsorption from the total amount of nucleic acid in the adsorption reaction system, and then used for calculating the elution effect. At pH 8.9, the elution effect of the nucleic acid adsorbed by FBD-MSP-ZEWA was greater than 85% while that of the nucleic acid adsorbed by the silanol magnetic bead (Thermo-Fisher Corporation) was lower than 30%, which supported the design concept of the invention.

Step (4)

Figure 10:
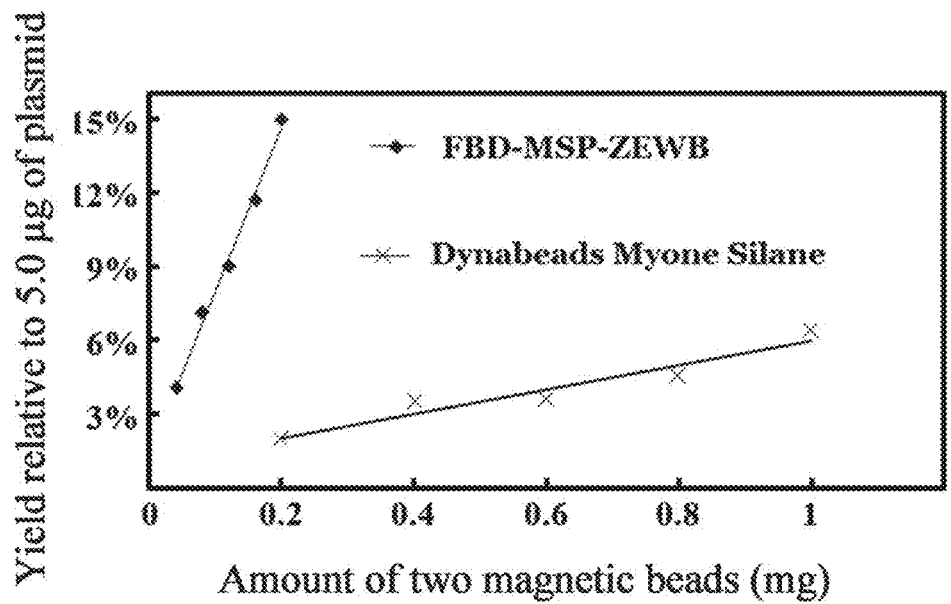
FIG. 10 shows response of the amount of plasmid separated to the amount of magnetic beads in the case of excess plasmid.

An adsorption system was 0.20 mL in total and contained 5.0 μg of a plasmid, and the eluent was 40 μL. A response curve of the obtained amount of nucleic acid to the amount of magnetic beads was shown in FIG. 10. It can be seen that the potency of FBD-MSP-ZEWB for separating nucleic acid may exceed 9 times that of the silanol magnetic bead (Thermo-Fisher Corporation). The separation capacity of FBD-MSP-ZEWB for nucleic acid was significantly higher than that of FBD-MSP-ZEWA, and the difference was consistent with the difference in the capacity of the two for separating acid red 13. Such difference also supported the design concept of the invention and the practicality of the designed ion exchanger.

Step (5)

Figure 11:
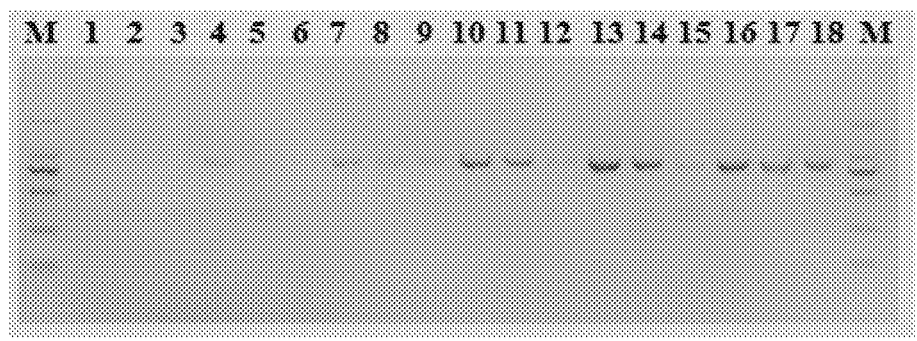
FIG. 11 shows semi-quantitative comparison of the efficacy of PCR after the plasmid is separated with magnetic beads and recycled in the case that the plasmid is not excessive.

An adsorption system was 0.20 mL in total and contained 0.40 μg of a plasmid. The adsorption system was separated by FBD-MSP-ZEWB (50 nmol, ~0.15 mg), silanol magnetic bead (1.0 mg, Thermo-Fisher Corporation) and silanol magnetic bead in a Biomiga kit (1.0 mg), respectively. The eluent was 40 μL. 2.5 μL of the nucleic acid extract was transferred to a PCR reaction system (50 μL). The PCR products obtained by different cycles or amplification times were detected by agarose electrophoresis, and the results were shown in FIG. 11, where M indicated the reference of the nucleic acid molecular weight; 1, 4, 7, 10, 13, 16: plasmids extracted by 0.15 mg of FBD-MSP-ZEWB; 2, 5, 8, 11, 14, 17: plasmids extracted by 1.0 mg of the silanol magnetic bead (Thermo-Fisher Corporation); 3, 6, 9, 12, 15, 18: plasmids extracted by 1.0 mg of the Biomigasilanol magnetic bead (the source of the silanol magnetic beads in the kit was unknown); 1, 2, 3: 10 PCR cycles in total; 4, 5, 6: 13 PCR cycles in total; 7, 8, 9: 16 PCR cycles in total; 10, 11, 12: 19 PCR cycles in total; 13, 14, 15: 22 PCR cycles in total; and 16, 17, 18: 25 PCR cycles in total.

As a template, the nucleic acid extracted by the FBD-MSP-ZEWB (50 nmol) showed significantly higher potency than that respectively extracted by 1.0 mg of the silanol magnetic bead (Thermo-Fisher Corporation) and 1.0 mg of the Biomigasilanol magnetic bead (the source of the silanol magnetic beads in the kit was unknown). The FBD-MSP-ZEWB was more suitable for extracting nucleic acids for PCR, supporting the application of the ion exchanger.

Example 5 Application of FBD-MSP-ZEWB in the Purification of Trace Recombinant RMGU-Expressing Protein by Ion Exchange MGU had a strong adsorption to carboxymethyl or phosphorylated cellulose and Toyopear sulfonic acid hydrophilic macroporous resin cation exchange medium, so that the adsorbed MGU cannot be eluted even using an eluent with a volume 10 times that of the gel (Protein J (2016) 35: 318-329, as a reference cited herein). The FBD-MSP-ZEWB, with a pIm close to 6.6 and differing from the pIs of RMGU by more than 2.0 pH units, was selected to improve the separation capacity of the amphoteric dissociation ion exchanger and ensure the stability of RMGU, so that a buffer solution with a pH between the pIm and the pIs and close to the neutrality was selected to lyse the cells and the lysed cells can be directly used for adsorption and separation after filtration with 0.22 m microporous membrane.

Step (1)

The cells were induced to express RMGU, lysed in the cell lysis solution 1 under ultrasonication and centrifuged at 12,000 rpm. The supernatant was filtered to give a recombinant RMGU-expressing crude enzyme sample, which had a protein content of 3.25 g/L, an activity of 3.27 kU/L and a specific activity of 1.01 kU/g.

Step (2)

Figure 12:
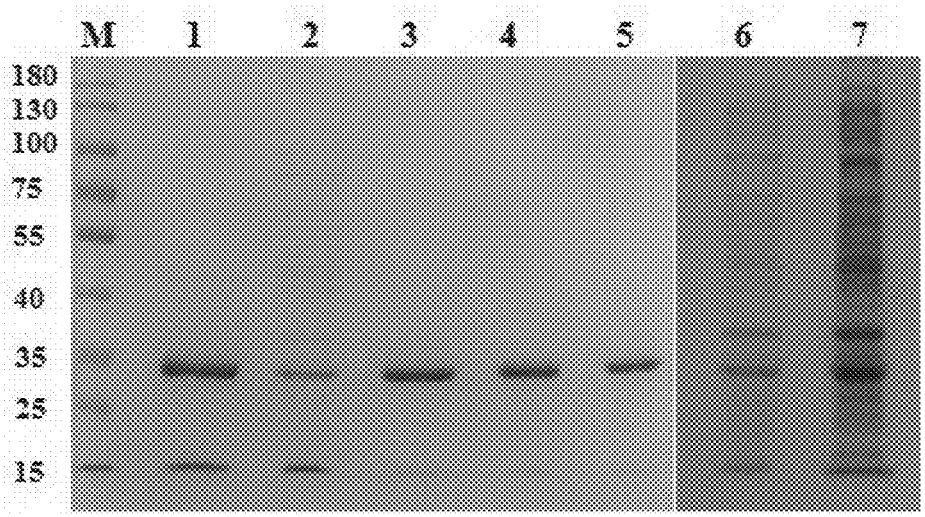
FIG. 12 shows SDS-PAGE analysis of the purification effect of FBD-MSP-ZEWB on *Pichiaguilliermondii* uricase RMGU. M: protein molecular weight Marker; 1: natural MGU, treated by DEAE-cellulose adsorption three times for removal of other proteins and purification and 5 μg for loading; 2:cell lysate, with a total protein of 5 μg for loading; 3: a lyophilized product of a second eluate obtained by elution with 0.20 mL of crude enzyme, 5 μg for loading; 4: a lyophilized product of a second eluate obtained by elution with 1.0 mL of crude enzyme, 5 μg for loading; 5: a lyophilized product of a second eluate obtained by elution with 4.0 mL of crude enzyme, 5 μg for loading; 6: a crude enzyme, with a total protein of 15 μg for loading; and 7: a crude enzyme, with a total protein of 45 μg for loading.

The FBD-MSP-ZEWB magnetic bead (3.0 μmol) was washed three times with the cell lysis solution, added with different amounts of the crude enzyme samples and mixed at room temperature for 10 minutes to produce a suspension. The suspension was separated magnetically. The resulting magnetic beads were washed with the cell lysis solution 1, added with the protein eluent 1 and mixed at room temperature for 30 minutes to give an eluate. After collecting the eluate, the magnetic beads were added with the same amount of the protein eluent 1 and re-eluted for 30 minutes. The elution was repeated several times. The concentration of the protein was determined by measuring the absorbance at 280 nm using Nanodrop, and the results were shown in Table 2. It can be seen that RMGU can be efficiently purified by FBD-MSP-ZEWB, and the specific activity of the resulting enzyme exceeded that of the enzyme purified by DEAE-cellulose adsorption three times (Protein J (2016)35:318-329). The highest elution efficacy of the adsorbed RMGU was nearly 80% when calculated according to the activity, while the MGU adsorbed by the classical cation exchange medium fails to be eluted. Moreover, the results of the batchwise elution with an eluent indicated that the RMGU with the highest activity and concentration was obtained by the second elution. Therefore, 80 μL of each of the second eluates was lyophilized, directly dissolved with a SDS-PAGE loading buffer (25 μL) under heating and analyzed by SDS-PAGE at the same loading amount of protein. The results showed that the purity of RMGU purified by FBD-MSP-ZEWB ion exchange once was very high and significantly higher than that of RMGU purified by DEAE-cellulose three times (FIG. 12; By comparison with Protein J (2016)35.318-329).

TABLE 2

Rapid separation of RMGU with FBD-MSP-ZEWB (3.0 μmol in total)
(ND indicated that the protein concentration was too low to detect)

| | Sample amount | | | | | |
|---|---|---|---|---|---|---|
| | 0.20 mL Crude enzyme | | 1.00 mL Crude enzyme | | 4.00 mL Crude enzyme | |
| Index | Activity (kU/L) | Protein concentration (g/L) | Activity (kU/L) | Protein concentration (g/L) | Activity (kU/L) | Protein concentration (g/L) |
| Supernatant after adsorption | 2.41 | 2.72 | 2.38 | 3.14 | 2.76 | 3.20 |

TABLE 2-continued

Rapid separation of RMGU with FBD-MSP-ZEWB (3.0 μmol in total)
(ND indicated that the protein concentration was too low to detect)

| | Sample amount | | | | | |
|---|---|---|---|---|---|---|
| | 0.20 mL Crude enzyme | | 1.00 mL Crude enzyme | | 4.00 mL Crude enzyme | |
| Index | Activity (kU/L) | Protein concentration (g/L) | Activity (kU/L) | Protein concentration (g/L) | Activity (kU/L) | Protein concentration (g/L) |
| Adsorbed amount (Expressed by activity/U or protein/μg) | 0.086 | 53 | 0.44 | 55 | 1.02 | 50 |
| The first eluate (0.20 mL) | 0.09 | ND | 0.20 | ND | 0.23 | ND |
| The second eluate (0.10 mL) | 0.32 | 0.028 | 0.57 | 0.053 | 0.71 | 0.09 |
| The third eluate (0.20 mL) | 0.08 | ND | 0.13 | ND | 0.13 | ND |
| Total activity of the eluates (U) | | 0.068 | | 0.13 | | 0.15 |
| Recovery rate of the activity after the elution (%) | | 79 | | 30 | | 15 |
| The highest specific activity of the eluate (kU/g) | | ~11.4 | | 10.8 | | 7.9 |
| Purification fold | | ~12.2 | | 10.6 | | 7.8 |

Example 6 Extraction of RMGU Plasmid with FBD-MSP-ZEWB for Quantitative PCR

Step (1)

E. coli cells were transformed with RMGU and then subjected to scale-up culture. The cells were collected, lysed with a base and extracted by a spin column method for a plasmid as a preliminarily-purified plasmid. The preliminarily-purified plasmid was adjusted to pH 3.6 with acetic acid (0.20 M) for subsequent purification.

Step (2)

The plasmid obtained in step (1) was further purified with FBD-MSP-ZEWB. The eluate was adjusted to pH 3.6 with acetic acid (0.20 M) and purified with FBD-MSP-ZEWB to give a plasmid standard, which was diluted to the appropriate concentration as described in Step (6).

Step (3)

FBD-MSP-ZEWB (50 nmol), DynabeadsMyoneSilane (1.0 mg) and Biomigakit magnetic beads (1.0 mg) were directly eluted with 40 μL of an eluent (25 mM Tris-HCl, pH 8.9), respectively, to obtain impurities from each of the magnetic beads.

Step (4)

The impurities from each of the magnetic beads were added with the same amount of the plasmid standard and used as the magnetic bead blank for fluorescence real-time quantitative PCR (qPCR) to compare the content of impurities, which can inhibit the qPCR, in the nucleic acids extracted by different magnetic beads.

Step (5)

The plasmid purified by the spin column was diluted. The diluted plasmid (20 μL, 0.40 μg) was adjusted to pH 3.6 with sodium acetate (45 μL, 0.20M) and acetic acid (235 μL, 0.20 M), respectively extracted with FBD-MSP-ZEWB (50 nmol, 0.15 mg), DynabeadsmyoneSilane (1.0 mg) and Biomiga kit magnetic beads (1.0 mg) and eluted with Tris-HCl buffer (40 μL, 25 mM, pH 8.9) to give test solutions of corresponding magnetic bead-extracted nucleic acid.

Step (6)

Samples for qPCR were listed as follows.

1—the plasmid standard

The RMGU plasmid was purified once by the spin column method and two times with FBD-MSP-ZEWB and determined to have a plasmid concentration of 26.9 mg/L by measuring the absorbance at 260 nm. The purified plasmid was diluted 1125 times with the eluent and used as an application liquid of the plasmid standard. The application liquid of the plasmid standard was diluted 4, 16, 64, 256 and 1024 times for qPCR, respectively.

2—FBD-MSP-ZEWB blank: prepared by an individual magnetic bead eluate (20 L, 50 nmol) and a 64-fold diluted application liquid of the plasmid standard (20 μL).

3—DynabeadsMyoneSilane blank: prepared by an individual magnetic bead eluate (20 μL, 1.0 mg) and a 64-fold diluted application liquid of the plasmid standard (20 μL).

4—Biomiga magnetic bead blank: prepared by an individual magnetic bead eluate (20 μL, 1.0 mg) and a 64-fold diluted application liquid of the plasmid standard (20 μL).

5—FBD-MSP-ZEWB test solution 0.40 g of the plasmid was extracted with 50 nmol of FBD-MSP-ZEWB magnetic beads and diluted 360 times with the eluent to give the FBD-MSP-ZEWB test liquid.

6—DynabeadsMyoneSilane test solution 0.40 g of the plasmid was extracted with 1.0 g of DynabeadsMyoneSilane and diluted 360 times with the eluent to give the DynabeadsMyoneSilane test liquid.

7—Biomiga magnetic bead test solution 0.40 g of the plasmid was extracted with 1.0 g of Biomiga magnetic bead and diluted 360 times with the eluent to give the Biomiga magnetic bead test solution.

Step (7)

Figure 13:
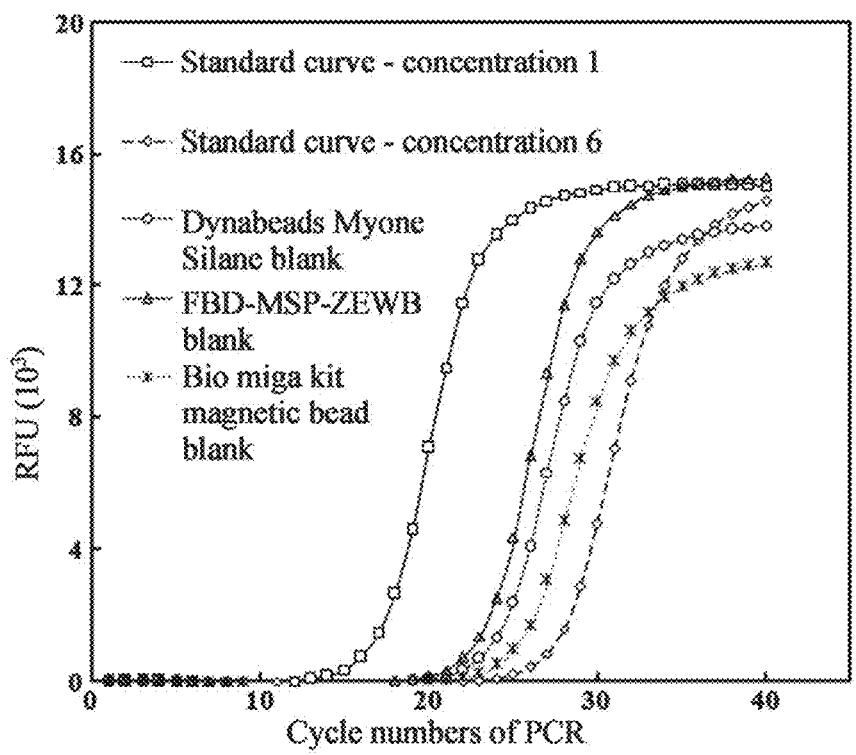
FIG. 13 shows the detection and comparison of fluorescence real-time quantitative PCR procedure for detecting interference from blank magnetic beads (see Example 7 for plasmid samples).
Figure 14:
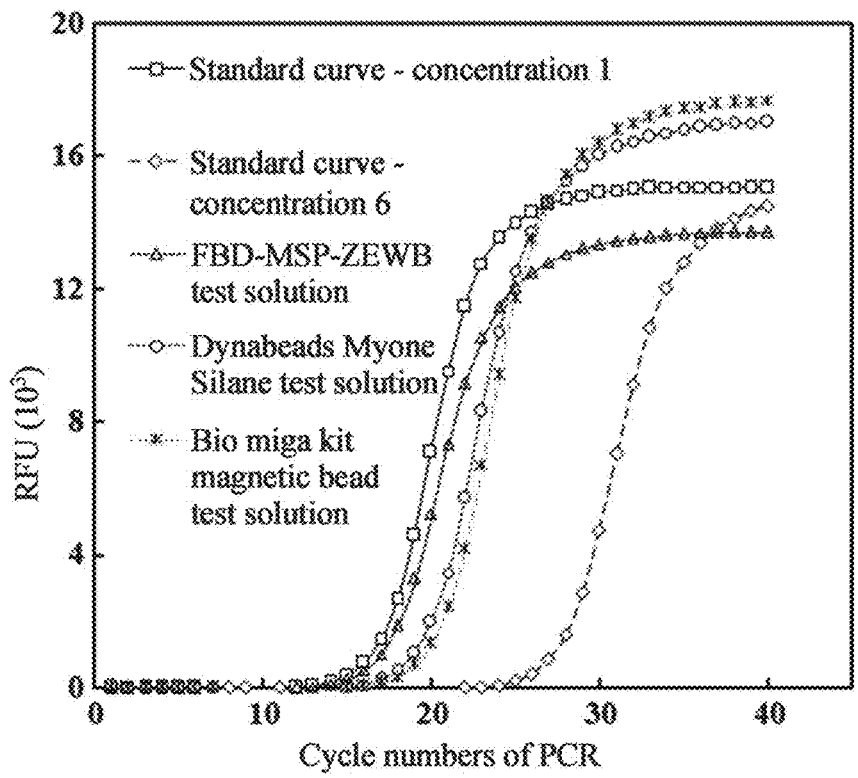
FIG. 14 shows the detection and comparison of fluorescence real-time quantitative PCR procedure for detecting the extraction of plasmids by magnetic beads (see Example 7 for plasmid samples).
Figure 15:
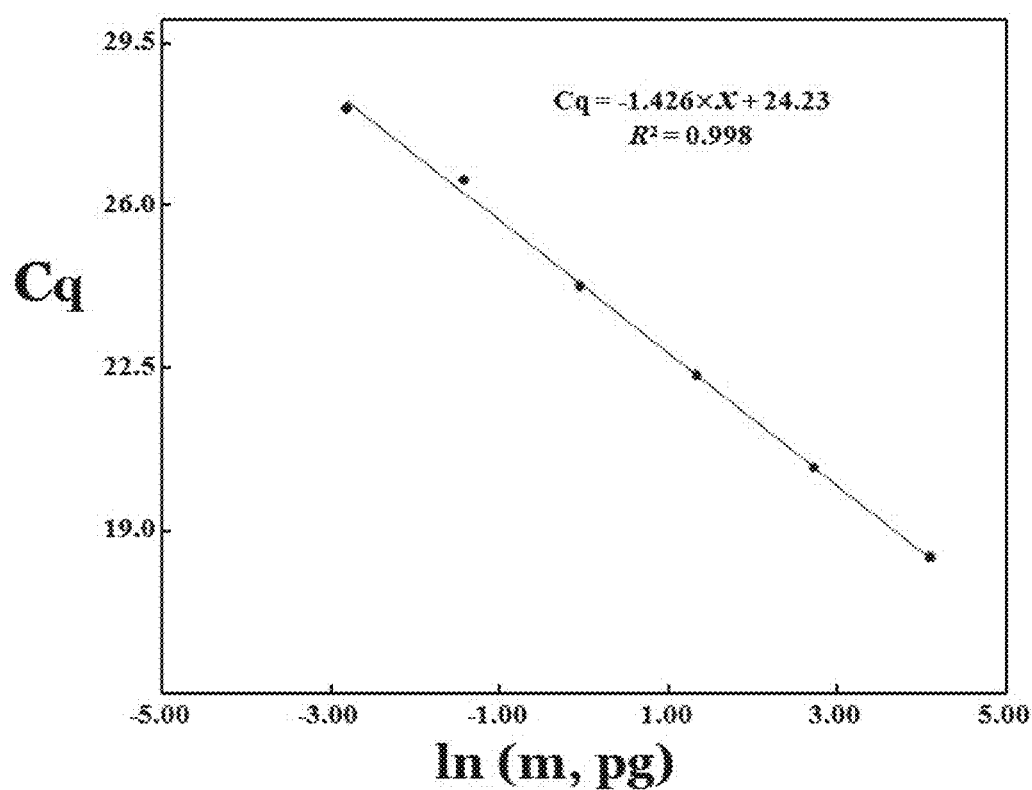
FIG. 15 shows the MGU expression plasmid response curve detected by fluorescence real-time quantitative PCR.

Fluorescence real-time quantitative PCR was performed as follows. BioradCFX96 was used according to the standard procedure; the fluorescent dye was Sybrgreen; and the PCR reaction system (25 μL in total) contained an enzyme, a trinucleotide, a primer for controlling the product to be 150 bp, Sybrlgreen and a template (2.5 μL). The process of tracing the magnetic bead blanks was shown in FIG. 13. The process of tracing the magnetic bead test solutions was shown in FIG. 14 and the response curve was shown in FIG. 15. The plasmid concentration in the application liquid of the plasmid standard was set to 24 pg/L, and the gradient of the total amount of the plasmid in each reaction system of the response curve was sequentially 60 pg, 15 pg, 3.75 pg, 0.94 pg, 0.24 pg and 0.06 pg, of which the natural logarithms were set as the abscissa to plot a negative response curve (see FIG. 15 for details).

Step (8)

It can be seen from Table 3 that when used for extracting nucleic acids, the impurities in the FBD-MSP-ZEWB showed the least inhibitory effect on PCR compared to those in the two silanol magnetic beads, and more inhibitory impurities were observed in the Biomiga magnetic beads. For a plasmid with a trace amount, given the amount of magnetic beads (mass) and the amount of a template for qPCR determination, the potency of the nucleic acid extracted by FBD-MSP-ZEWB for qPCR exceeded 10 times that of the nucleic acid extracted by DynabeadsMyone Silane for qPCR. The Biomiga magnetic bead treatment resulted in the lowest template amount after qPCR due to the obviously more impurities inhibiting qPCR.

ration medium for PCR was near 10 times that of the nucleic acid extracted by the Thermo-Fisher DynabeadsMyone Silane silanol magnetic beads.

Finally, the above examples are merely illustrative of the technical solutions of the invention and are not intended to limit the scope of the invention. It should be understood that modifications and equivalent substitutions made by those skilled in the art without departing from the spirit and scope of the invention should fall within the scope as defined by the appended claims.

We claim:

1. A method for calibrating separation capacity of amphoteric dissociation ion exchange magnetic beads, wherein a surface of the amphoteric dissociation ion exchange magnetic beads is an amphoteric dissociation covalently-modified layer; the amphoteric dissociation covalently-modified layer has an isoelectric point (pIm) that is an environmental pH value at which a net charge on the surface of the amphoteric dissociation ion exchange magnetic beads is zero; and the method comprises:

a) selecting a colored organic compound as a color-developing probe for the calibration of the separation capacity of the amphoteric dissociation ion exchange magnetic beads; wherein the colored organic compound has a dissociation constant of pK or an isoelectric point of pI, a molecular weight less than 600 Daltons, a visible light absorption coefficient greater than 14 mM$^{-1}$·cm$^{-1}$, a solubility not less than 5.0 μmol/L at pH 3.0-11.0, and a positive or negative net charge after dissociation at pH 3.0-11.0; and the color-developing probe is a cationic probe or an anionic

TABLE 3

Determination of the amount of plasmid extracted by magnetic beads and interfering impurities in various magnetic bead extracts by fluorescence real-time quantitative PCR

| Samples | Dynabeads-Myone Silane Blank | FBD-MSP-ZEWB Blank | Biomiga magnetic bead blank | Dynabeads-Myone Silane test solution | FBD-MSP-ZEWB test solution | Biomiga magnetic bead test solution |
|---|---|---|---|---|---|---|
| Cq | 25.56 | 24.45 | 25.74 | 20.46 | 18.60 | 21.01 |
| Plasmid amount (pg) | 0.43 | 0.94 | 0.35 | 14.09 | 51.88 | 9.58 |
| Ratio to Dyna | 1.0 | 2.2 | 0.81 | 1.0 | 3.7 | 0.68 |

The above examples demonstrated the practicality of the amphoteric dissociation ion exchange separation medium of the invention. The media had strong adsorption and elution properties for acid red 13 dyes, so that acid red 13 can be used for characterizing the ion exchange separation medium and the separation medium can also be used to recycle and reuse the acid red water-soluble dyes in printing and dyeing waste liquid. The elution and measurement which were performed based on the binding of the ion exchange separation medium to acid red 13 can facilitate the characterization of the pIm of the prepared amphoteric dissociation ion exchange separation medium and pH effect of the eluent. The amphoteric dissociation ion exchange separation medium with an appropriate pIm can be used to efficiently and rapidly purify the protein and efficiently extract nucleic acids. Moreover, the extracted nucleic acids were more suitable for PCR. The results of the fluorescence real-time quantitative PCR indicated that based on the mass of the micro-magnetic beads, the potency of the nucleic acid extracted by the amphoteric dissociation ion exchange sepaprobe, wherein the cationic probe has a dissociation constant of DK or an isoelectric point of pI at least 2.0 greater than the pIm of the amphoteric dissociation ion exchange magnetic beads, and the anionic probe has a dissociation constant of pK or an isoelectric point of pI at least 2.0 lower than the pIm of the amphoteric dissociation ion exchange magnetic beads;

b) calibrating the separation capacity of the amphoteric dissociation ion exchange magnetic beads; wherein step b comprises:

b1) when the amphoteric dissociation ion exchange magnetic beads have an isoelectric point pIm between 4.0 and 6.0, using the cationic probe or the anionic probe; and b2) when the amphoteric dissociation ion exchange magnetic beads have the pIm between 6.0 and 10.0, using the anionic probe;

c) when calibrating the separation capacity of the amphoteric dissociation ion exchange magnetic beads, selecting a first buffer solution corresponding to an environmental pH, wherein the environmental pH is between the dissociation constant pK or the isoelectric point pI of the color-developing probe and the pIm of the amphoteric dissociation ion exchange magnetic beads, and differs from the pIm of the amphoteric dissociation ion exchange magnetic beads by not less than 1.3 and differs from the dissociation constant pK or the isoelectric point pI of the color-developing probe by not less than 0.5; dissolving the color-developing probe in the first buffer solution; suspending the amphoteric dissociation ion exchange magnetic beads in the first buffer solution that contains the color-developing probe to obtain a first suspension, in which the amphoteric dissociation ion exchange magnetic beads adsorb the color-developing probe by electrostatic attraction; magnetically separating a mixture of the amphoteric dissociation ion exchange magnetic beads and the color-developing probe adsorbed on the amphoteric dissociation ion exchange magnetic beads from the first suspension to obtain the mixture; selecting a second buffer solution corresponding to an environmental pH, wherein the environmental pH is at least 1.3 higher than the higher one or at least 1.3 lower than the lower one of the dissociation constant pK or the isoelectric point pI of the color-developing probe and the pIm of the amphoteric dissociation ion exchange magnetic beads; suspending the mixture in the second buffer solution to obtain a second suspension, in which the type of net charges on the surface of the amphoteric dissociation ion exchange magnetic beads is the same as that of the color-developing probe to dissociate the color-developing probe from the amphoteric dissociation ion exchange magnetic beads by electrostatic repulsion; magnetically removing the solid ion-exchange magnetic beads from the second suspension to obtain a supernatant containing the color-developing probe; measuring the absorbance of the color-developing probe in the supernatant containing the color-developing probe; and converting the absorbance of the color-developing probe to a separation capacity to the color-developing probe according to Beer-Lambert law.

* * * * *